(12) United States Patent
Cowan et al.

(10) Patent No.: US 7,462,166 B2
(45) Date of Patent: *Dec. 9, 2008

(54) ENCODING AND SENSING OF SYRINGE INFORMATION

(75) Inventors: Kevin P. Cowan, Allison Park, PA (US); Barry Iddon, Jeannette, PA (US); Michael J. Yanniello, Cheswick, PA (US); John A. Brosovich, Pittsburgh, PA (US); Alan D. Hirschman, Glenshaw, PA (US)

(73) Assignee: Medrad, Inc., Indianola, PA (US)

( * ) Notice: Subject to any disclaimer, the term of this patent is extended or adjusted under 35 U.S.C. 154(b) by 420 days.

This patent is subject to a terminal disclaimer.

(21) Appl. No.: 10/466,418

(22) PCT Filed: Jan. 16, 2002

(86) PCT No.: PCT/US02/01052

§ 371 (c)(1),
(2), (4) Date: Jul. 16, 2003

(87) PCT Pub. No.: WO02/056934

PCT Pub. Date: Jul. 25, 2002

(65) Prior Publication Data

US 2004/0064101 A1 Apr. 1, 2004

(51) Int. Cl.
*A61M 37/00* (2006.01)

(52) U.S. Cl. .................................................. 604/131

(58) Field of Classification Search ................ 604/111, 604/118, 131, 189, 154, 151, 218, 49, 65, 604/67, 93.01, 121, 152, 181, 187; 128/DIG. 1, 128/DIG. 12; 116/227; 235/375, 435, 448, 235/454, 462; 600/431, 432
See application file for complete search history.

(56) References Cited

U.S. PATENT DOCUMENTS 4,006,736 A 2/1977 Kranys et al.

(Continued)

FOREIGN PATENT DOCUMENTS

| WO | WO 97/36635 | 10/1997 |
|---|---|---|
| WO | WO 98/00187 | 8/1998 |
| WO | WO 99/65548 | 12/1999 |
| WO | WO 01/08727 | 2/2001 |
| WO | WO 01/37903 | 5/2001 |
| WO | WO 02/056934 | 7/2002 |
| WO | WO 02/081011 | 10/2002 |

OTHER PUBLICATIONS

Redacted Post-Claim Construction Declaration of Thomas H. Braunstein (Nov. 19, 2001).

(Continued)

*Primary Examiner*—Matthew F Desanto
(74) *Attorney, Agent, or Firm*—Jill Denesvich; Gregory L. Bradley; Henry E. Bartony, Jr.

(57) ABSTRACT

A syringe for use with a powered injector to inject a fluid into a patient inclides an encoder. The encoder includes at least a first indicator positioned on the encoder. The first indicator is adapted to interact with at least a portion of energy being propagated through or adjacent the encoder in a manner that is detectable. The presence (or absence) of the first indicator provides or corresponds to information about the syringe configuration. The indicator(s) of the present invention can, for example, provide information about syringe configuration by the number and/or position thereof. A plurality or set of such syringes can be provided, with the configuration of each such syringe being represented by the presence or absence of indicator(s) of that syringe.

35 Claims, 33 Drawing Sheets

U.S. PATENT DOCUMENTS

| | | | |
|---|---|---|---|
| 4,278,086 A | | 7/1981 | Hodgins et al. |
| 4,650,475 A | | 3/1987 | Smith et al. |
| 4,978,335 A | | 12/1990 | Arthur, III |
| 5,066,859 A | * | 11/1991 | Karkar et al. .......... 250/339.09 |
| 5,383,858 A | | 1/1995 | Reilly et al. |
| 5,520,653 A | | 5/1996 | Reilly et al. |
| 5,531,698 A | | 7/1996 | Olsen |
| 5,545,140 A | * | 8/1996 | Conero et al. ............... 604/154 |
| 5,662,612 A | | 9/1997 | Niehoff |
| 5,741,232 A | | 4/1998 | Reilly et al. |
| 5,873,861 A | | 2/1999 | Hitchins et al. |
| 5,928,197 A | | 7/1999 | Niehoff |
| 5,944,694 A | | 8/1999 | Hitchins et al. |
| 5,954,700 A | | 9/1999 | Kovelman |
| 5,997,502 A | | 12/1999 | Reilly et al. |
| 6,004,292 A | * | 12/1999 | Battiato et al. .............. 604/123 |
| 6,019,745 A | | 2/2000 | Gray |
| 6,090,064 A | | 7/2000 | Reilly et al. |
| 6,533,183 B2 | | 3/2003 | Aasmul et al. |
| 6,958,053 B1 | * | 10/2005 | Reilly ........................ 604/154 |
| 7,018,363 B2 | * | 3/2006 | Cowan et al. ............... 604/181 |
| 2001/0034506 A1 | | 10/2001 | Hirschman |
| 2002/0000471 A1 | | 1/2002 | Aasmul et al. |
| 2002/0128606 A1 | | 9/2002 | Cowan et al. |
| 2003/0060754 A1 | | 3/2003 | Reilly et al. |
| 2003/0065287 A1 | | 4/2003 | Spohn et al. |

OTHER PUBLICATIONS

International Search Report for Counterpart PCT Application No. PCT/US02/01052.

International Search Report for PCT Application No. PCt/US02/10398.

Post-Claim Construction Declaration of Thomas H. Braunstein (Nov. 19, 2001).

Second Post-Claim Construction Declaration of Thomas H. Braunstein (Dec. 7, 2001).

* cited by examiner

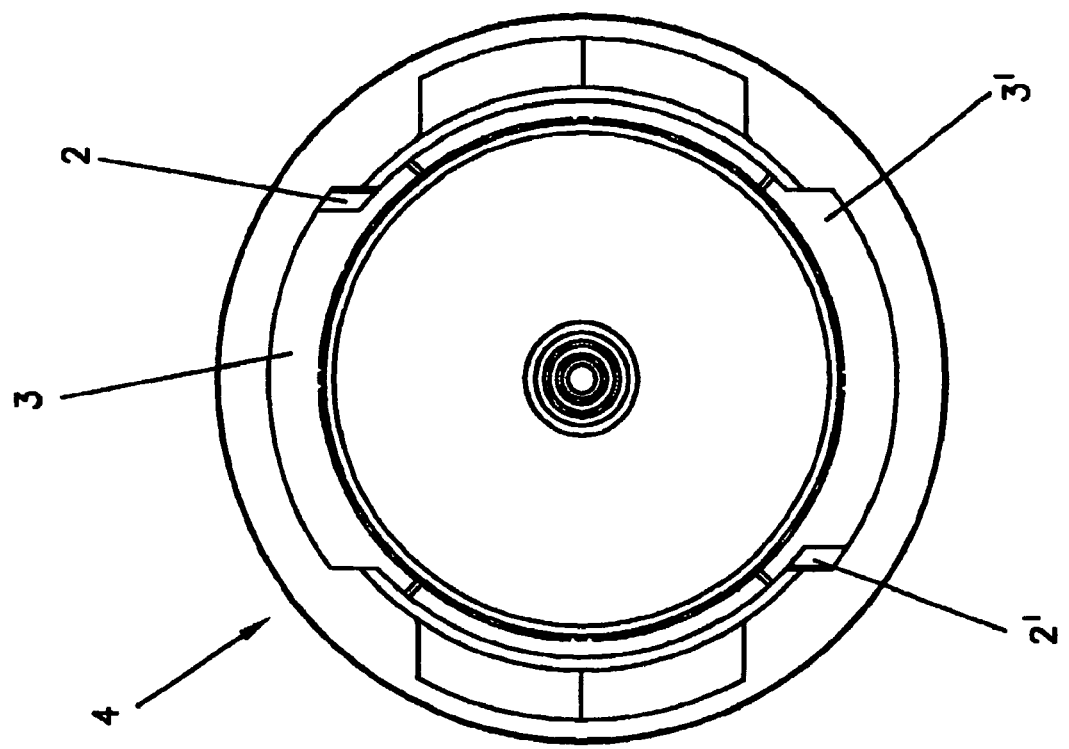

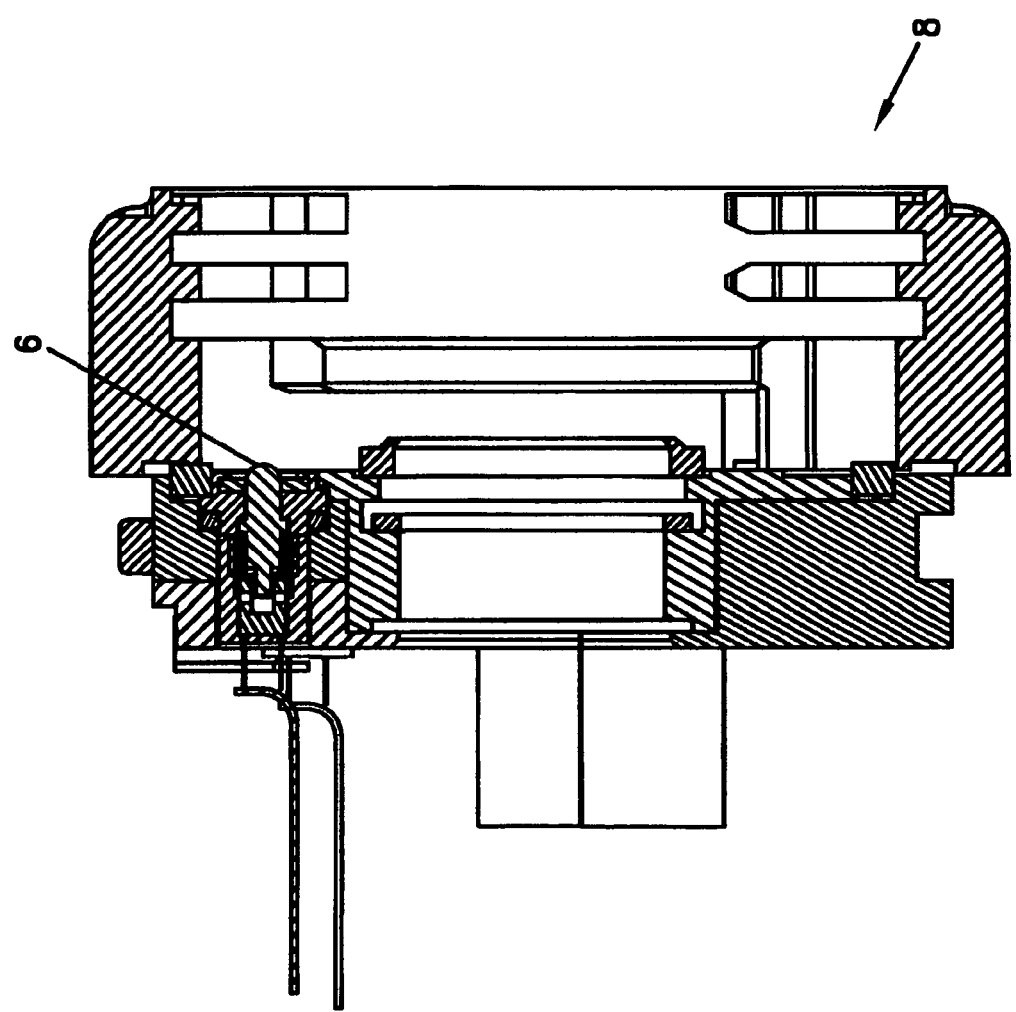

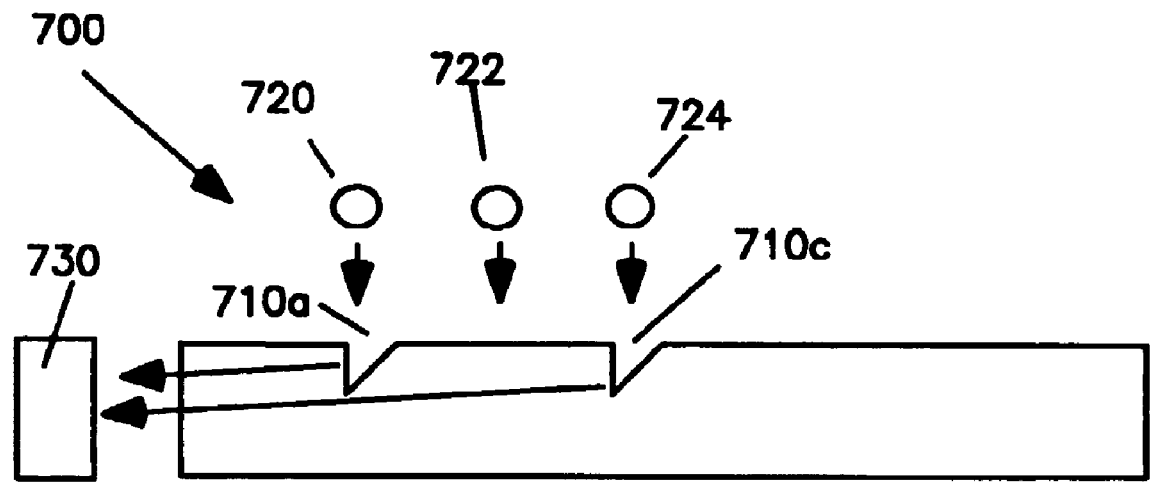
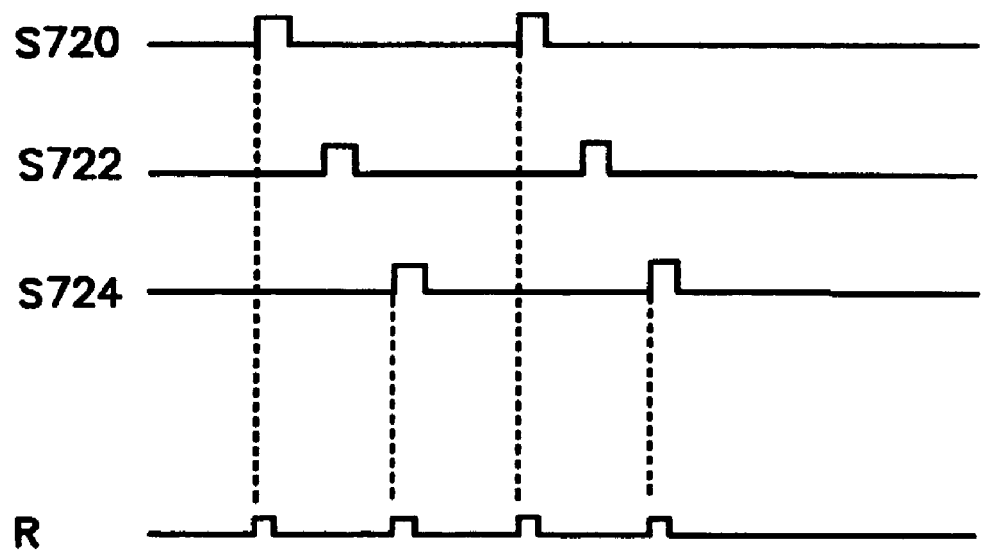
FIG. 6

ENCODING AND SENSING OF SYRINGE INFORMATION

BACKGROUND OF THE INVENTION

The present invention relates to encoding and sensing of information or configuration, and, especially, to syringes and syringe encoders having encoding of information relevant to medical injection procedures, to injector systems including syringe encoding and to methods of encoding and sensing syringe information.

Critical parameters of an injection procedure are determined by a number of variables, including, for example, syringe diameter, syringe length, syringe material and fluid composition/concentration. Among the affected injection procedure parameters are fluid volume delivered, flow rate, fluid pressure, and limits of injector piston travel. In current injector systems, syringe size is generally determined either (1) manually by action of an operator who enters the syringe size or type into the injector software, or (2) automatically by means of switches on the injector head which are mechanically coupled to raised or sunken elements on the syringe. See, for example, U.S. Pat. Nos. 5,741,232, 6,090,064 and 5,873,861, assigned to the assignee of the present application, the disclosures of which are incorporated herein by reference. FIG. 1A illustrates sunken elements or detents 2 and 2' positioned around the arc of flanges 3 and 3' in a rear, engagement flange portion of a syringe 4 as described in U.S. Pat. No. 5,873,861. Syringes 4, including detents 2 and 2', have been fabricated from, for example, clear or opaque, polymeric materials. Detents 2 and/or 2' cooperate with one or more correspondingly positioned switches 6 in a powered injector 8 illustrated in FIG. 1B. The presence or absence of one or more of detents provides a code that represents syringe configuration.

Constraints of mechanical and electrical design, however, limit the number of such automatic detection switches. Indeed, only limited syringe configurations are automatically detected with present systems. Additionally, failure of moving mechanisms is also a problem. Moreover, certain electrical and mechanical encoding systems can significantly increase manufacturing costs of a syringe and/or injector. Other currently available methods of encoding and sensing syringe configuration include the placement of bar codes and corresponding sensors upon the syringe and injector, respectively, as disclosed in U.S. Pat. No. 5,997,502. Bar code systems, however, suffer from some of the same problems as the electromechanical systems discussed above.

As used herein, the term "syringe configuration" is used to encompass all information about a particular syringe, including, but not limited to, information about the mechanical properties of a syringe (for example, material, length and diameter) as well as information about the contents of the syringe (for example, volume and composition). With the advent of new syringes, and especially prefilled syringes, the need to accurately encode and sense (or read) syringe configuration variables is heightened. The syringe configuration information can be used by a powered injector to control the injection procedure as a function of defined syringe configuration/injection parameters. Moreover, a record of data associated with an injection procedure may be kept, for example, to satisfy accurate billing and cost information requirements under managed health care. A record may be maintained of information such as the type of syringe used, the amount of contrast medium used, the type of contrast medium used, the sterilization date, the expiration date, lot codes, the properties of the contrast media, and/or other clinically relevant information. Such information can be recorded digitally for sharing with computerized hospital billing systems, inventory systems, control systems, etc.

SUMMARY OF THE INVENTION

In general, the present invention provides for encoding and sensing of information by providing one or more indicators that interact with electromagnetic energy in a manner that is detectable. In a number of embodiments, the electromagnetic energy is light energy. The electromagnetic energy can, for example, be propagated through a length of material in which the indicator(s) are formed or be propagated through a medium surrounding the material in which the indicator(s) are formed.

In one aspect, for example, the present invention provides a syringe for use with a powered injector to inject a fluid into a patient that includes a length of material adapted to transmit or propagate electromagnetic energy therethrough or through the length thereof. The length of material includes at least a first indicator positioned along the length of material. As described above, the first indicator is adapted to interact with at least a portion of the energy propagated through the length of material in a manner that is detectable.

The presence (or absence) of the first indicator provides or corresponds to information about the syringe configuration in the above embodiment. The indicator(s) of the present invention can, for example, provide information (for example, about syringe configuration) by the number and/or position thereof. A plurality or set of encoded articles (for example, syringes) can be provided, with the configuration of each article being represented by the presence, absence and/or positioning of indicator(s) of that article.

As used herein with respect to the information provided by the indicators, the terms "position," "positioning" and related terms refer to absolute and/or relative position. In that regard, information can be provided by the absolute position of one or more indicators upon an encoded article (for example, upon the length of material of the syringe described above). As used herein, the term absolute position refers to the position of the indicator(s) on or within the article or length material with respect to a reference position (for example, a fixed position on the length of material or on a powered injector). Information can also be provided by the relative positions of a plurality of indicators with respect to each other independent of their absolute positions upon the article or the length of material.

As used herein in connection with electromagnetic energy transmitted or propagated to contact or impinge upon the indicators of an encoded article or length of material, the phrase "interact with" refers generally to, for example, a transmission of the energy, a change in the direction of the energy, a change in the intensity of the energy, a change in the speed of travel of the energy and/or a change in form of the energy. Such interactions are preferably readily detectable, for example, using sensors as known in the art. For example, the indicator can be adapted to transmit the energy impinging thereupon without modification thereof, or can be adapted to transform, refract, scatter and/or absorb at least a portion of the energy. In general, the indicators of the present invention are discontinuities or areas having properties different from the remainder of the encoded article or length of material such that the energy impinging upon an indicator interacts differently from energy that impinges upon a portion of the encoded article or length of material not including an indicator. This different interaction of the indicator with impinging energy is detectable. For example, in the case of energy propagated through a length of material, an indicator can be an area of the length of material through which energy can be transmitted outside of the length of material whereas the remainder of the length of material prevents transmission of energy outside of length of material. In the case of light energy, for example, indicators can be discontinuities such as angled surfaces formed in the encoded article or length of material that, for example, refract, reflect, scatter or absorb light energy. Indicators can also include a detection material (for example, a fluorescent material) that is placed in a detectible state upon impingement of the energy.

Preferably, the syringe (or other encoded article) includes a plurality of indicators (that is, preferably at least two indicators) along the encoded article or length of the material positioned at unique predetermined positions (that is, absolute and/or relative positions). Each of the indicators is adapted to interact with or to modify at least a portion of the energy impinging thereon. The number of indicators can provide information of syringe configuration. Likewise, predetermined positions of the indicators can provide information about syringe configuration. For example, a binary/digital code can be set forth by the presence/absence of indicators at predetermined positions. Multiple, binary codes can be placed on a single syringe or other encoded article using groups or sets of indicators at different positions upon the syringe or other encoded article.

In one embodiment, the electromagnetic energy is light energy and the length of material can, for example, have a refractive index greater than the refractive index of an adjacent environment such that light energy can be internally reflected in the material along its length. Internal reflectance assists in efficiently propagating light energy through the length of the material. Indicators suitable for use with light energy include, for example, angled surfaces in the syringe wall adapted to refract and/or reflect light energy to a sensor or sensors.

The length of material can, for example, be formed integrally with the syringe or other encoded article. In one such embodiment, the length of material is a translucent portion of the syringe wall. Likewise, the length of material can also be separate from the syringe or other encoded article. The length of material can, for example, be associated with or attachable to the syringe. The length of material can also form part of a syringe adapter designed to adapt a syringe for use with a particular injector or part of a heater jacket used to warm contrast within a syringe as known in the art.

In another aspect, the present invention provides a syringe encoder for use with a powered injector to inject a fluid into a patient. The syringe encoder includes a length of material adapted to transmit or propagate electromagnetic energy therethrough. The length of material includes at least a first indicator positioned along the length of material. As discussed above, the first indicator is adapted to interact with at least a portion of the energy being transmitted or propagated through the length of material in a manner that is detectable to provide information about the syringe configuration. The syringe encoder can, for example, be formed integrally with, be associated with (for example, shipped in the same container), or be attachable to a syringe or a syringe adapter (designed to adapt a particular syringe for use with a powered injector).

In another aspect, the present invention provides an injector system for use with a syringe. The injector preferably includes a drive member, at least one source of electromagnetic energy and at least one sensor. The injector system further includes a syringe encoder as described above. In that regard, the syringe encoder includes a length of material adapted to transmit or propagate electromagnetic energy therethrough. The length of material includes at least a first indicator along the length of material that is adapted to interact with at least a portion of the energy transmitted or propagated through the length of material in a manner that is detectable by the sensor.

In another aspect, the present invention provides an encoder system including at least one source of electromagnetic energy and at least one sensor. The encoder system further includes a syringe encoder as described above. In that regard, the syringe encoder includes a length of material adapted to propagate electromagnetic energy therethrough. The length of material includes at least a first indicator along the length of material that is adapted to interact with at least a portion of the energy being transmitted or propagated through the length of material in a manner that is detectable by the sensor.

In a further aspect, the present invention provides a method of encoding information about syringe configuration. The method includes the steps of: transmitting or propagating energy through a least a portion of a length of material; providing at least a first indicator adapted to interact with at least a portion of the energy being transmitted or propagated through the length of material in a manner that is detectable along the length of material; and detecting the interaction of at least a portion of the energy with the first indicator. As described above, a predetermined position of one or more indicators can be used to provide information about syringe configuration.

The encoders and methods of the present invention are not limited to use with syringes or in medical injection procedures. Such encoders can be used with other pumps, pressurizing mechanisms or other fluid path elements used in medical injection procedures, such as the pumps and fluid path elements disclosed, for example, in U.S. Pat. Nos. 5,806,519, 5,843,037 and 5,916,197, assigned to the assignee of the present invention, the disclosures of which are incorporated herein by reference. Indeed, the encoders and methods of the present invention are well suited for any use in which it is desirable to encode information in the medical arts or in other fields of use. In another aspect, the present invention thus provides an encoder including a length of material adapted to transmit or propagate electromagnetic energy therethrough. The length of material includes at least a first indicator positioned along the length of material. As discussed above, the first indicator is adapted to interact with at least a portion of the energy being transmitted or propagated through the length of material in a manner that is detectable to provide information.

Likewise, the present invention provides a method of encoding information including the steps of: transmitting or propagating energy through a least a portion of a length of material; providing at least a first indicator adapted to interact with at least a portion of the energy being transmitted or propagated through the length of material in a manner that is detectable along the length of material; and detecting the interaction of at least a portion of the energy with the first indicator. As described above, a predetermined position (relative position and/or absolute position) of one or more indicators can be used to provide information.

In addition to propagation of energy through the length of an encoded article or length of material, electromagnetic energy can also be propagated around or adjacent to an encoded article or length of material in which indicators of the present invention are formed or positioned in a manner to impinge upon the indicators.

In that regard, in a further aspect the present invention provides a syringe including at least a first indicator positioned along the syringe wall. The first indicator interacts with at least a portion of energy being propagated adjacent to the syringe wall and generally parallel to the syringe axis in a manner that is detectable to provide information about the syringe configuration. A plurality of such indicators can be provided along the length of the syringe wall at unique predetermined longitudinal positions. Each of the indicators interacts with at least a portion of the energy being propagated adjacent the syringe wall in a manner that is detectable. The predetermined positions of the indicators provide information about the syringe configuration.

Each of the indicators can, for example, have a different radial position. In one embodiment, a plurality of indicators is formed as a stepped progression.

In another aspect, the present invention provides a syringe encoder including a length of material that interacts with electromagnetic energy. The length of material includes at least a first indicator positioned along the length of material to interact at least a portion of the energy being propagated generally across a surface of the length of material in a manner that is detectable. The first indicator provides information about syringe configuration.

In a further aspect, the present invention provides a method of fabricating a syringe for use with a powered injector to inject a fluid into a patient. The method includes the step of forming at least a first indicator along the length of the syringe as described above. As also described above, at least a first plurality of indicators can be formed along the length of the syringe wall at unique predetermined longitudinal positions. The indicators can, for example, include a surface formed in the wall of the syringe to transmit light energy traveling along a surface of the syringe to a corresponding sensor.

In another aspect, the present invention provides a method of encoding information about syringe configuration. The method comprises the steps of: propagating energy generally adjacent a wall of the syringe and generally parallel to the axis of the syringe; providing at least a first indicator positioned along the syringe wall, the first indicator being adapted to interact with at least a portion of the energy being propagated adjacent the syringe wall in a manner that is detectable; and detecting the modification of at least a portion of the energy, the indicator providing information about syringe configuration.

In another aspect, the present invention provides a set of at least two syringes for use with a powered injector to inject a fluid into a patient. Each syringe includes a length of material including at least one indicator positioned along a surface of the length of material. The at least one indicator of each syringe interacts with at least a portion of the energy being propagated generally along the surface of the length of material in a manner that is detectable. The indicator(s) of each syringe provide information about a unique configuration of the syringe upon which the indicator(s) are positioned.

In a further aspect, the present invention provides an encoder including a length of material having at least a first indicator positioned along a surface of a length of material. As described above, the first indicator interacts at least a portion of the energy being propagated along the surface of the length of material in a manner that is detectable to providing encoded information. The present invention provides in another aspect an injector system including a syringe encoder as described above.

In a further aspect, the present invention provides a method of encoding information. The method includes the steps of: propagating light energy along a surface of a length of material; providing at least a first indicator positioned along the length of material to interact with at least a portion of the light energy being propagated along the surface of the length of material in a manner that is detectable; and detecting the interaction of at least a portion of the energy.

The present invention provides in a further aspect a syringe for use with a powered injector to inject a fluid into a patient. The syringe includes a length of material including a plurality of indicators formed along the length of a surface of the length of material. Each of the indicators includes a first, generally flat surface that is angled with respect to an orientation of light propagated along the surface of the length of material to redirect at least a portion of the light in a manner that is readily detectable. Each indicator can, for example, include a step change in radius along the length of material. The step change in radius includes an angled surface that reflects a portion of the light.

In another aspect, the present invention provides a method of fabricating syringes with encoded information. The method includes the step of forming a plurality of indicators along a length of material associated with a syringe. Each of the indicators includes a generally flat surface that is angled with respect to an orientation of light to be propagated along the surface of the length of material to redirect at least a portion of the light to be detected.

In another aspect, the present invention provides a syringe including a syringe wall having at least a first indicator positioned along a surface of the syringe wall to interact with at least a portion of light energy being propagated along the surface of the syringe wall in a manner that is detectable. The syringe can, for example, include at least a first plurality of indicators positioned along the surface of the syringe wall at different longitudinal positions and representing a binary code providing information about the syringe configuration.

The syringe wall can, for example be generally cylindrical in shape. Further, the syringe can include at least a first plurality of indicators aligned along the syringe wall at different longitudinal positions such that a beam of light from a single light source can be propagated along the surface of the syringe wall in a direction generally parallel to the axis of the syringe to interact with each of the first plurality of indicators.

In still a further aspect, the present invention provides a sensor assembly for use in a powered injector. The sensor assembly includes a positioning subassembly having a translucent surface through which light can pass and at least one abutment member spaced from the translucent surface. The abutment member operates to position an encoded syringe or syringe adapter seated in a gap formed between the translucent surface and the abutment member at a desired position relative to the translucent surface. For example, the syringe or syringe adapter can be positioned sufficiently closely to the translucent surface to prevent formation of fluid droplets between the syringe or syringe adapter and the translucent surface.

The sensor assembly preferably further includes at least one sensor positioned on the side of the translucent surface opposite the side upon which the abutment member is positioned. More preferably, the sensor assembly preferably includes a plurality of sensors positioned on the side of the translucent surface opposite the side upon which the abutment member is positioned. The sensor assembly also preferably includes a light source positioned to transmit light in an axial direction in the gap formed between the translucent surface and the abutment member. In one embodiment, a testing light source is provided for each sensor to test the operability of each sensor.

The present invention also provides in another aspect an injector for use with an encoded syringe or an encoded syringe adapter. The injector includes an interface to attach the syringe or the syringe adapter to the powered injector; a drive member to impart motion to a syringe plunger, at least one light source to propagate light in an axial direction, and at least one sensor to detect light impinging thereupon as a result of the encoding of the syringe or the syringe adapter. The injector can also include a sensor assembly as described above.

The encoding schemes of the present invention provide a reliable manner of encoding information of, for example, syringe configuration. Mechanically movable mechanisms are not required, resulting in increased reliability as compared to many prior art encoding schemes. Moreover, the syringe encoders of the present invention are readily formed integrally with, for example, a syringe or a syringe adapter, resulting in less costly manufacture than many prior encoding mechanisms.

Furthermore, the encoding systems, devices and methods of the present invention are well suited for use in magnetic resonance environment in which care must be taken to prevent failure of the encoding system or device and to prevent interference with the magnetic resonance imaging equipment. In that regard, the strong magnetic field in a magnetic resonance environment can adversely affect certain types of devices such as electromechanically activated devices. Furthermore, differences in magnetic permeability of materials within such devices and induced eddy currents therein can affect the homogeneity of the MRI magnetic field, generating image artifacts. Likewise, radio frequency energy generated by certain devices can induce unwanted artifacts upon the acquired MRI images. Such problems are easily avoided in the syringe encoding systems, devices and methods of the present invention. For example, electromechanical and other actuators are unnecessary in the present invention as no moving elements are required. Moreover, electromechanical energy used in the encoding systems, devices and methods of the present invention is easily selected to prevent interference with magnetic resonance equipment as well as interference from the magnetic resonance equipment. For example, light energy in the infrared, visible or ultraviolet range of the spectrum can be used. Likewise, radio frequency energy outside of frequency range of the MRI scanner can be used.

The present invention and its attendant advantages will be further understood by reference to the following detailed description and the accompanying drawings.

BRIEF DESCRIPTION OF THE DRAWINGS

FIG. 1A illustrates a rear plan view of a currently available syringe including detents for providing syringe configuration information.

FIG. 1B illustrates a side cross-sectional view of the front portion of a currently available injector including electromechanical switches to cooperates with the detents of FIG. 1A.

FIG. 6 illustrates a side cross-sectional view of a syringe encoding system in which energy signals are pulsed.

DETAILED DESCRIPTION OF THE INVENTION

The encoders, encoding systems and encoding methods of the present invention are particularly useful in encoding information of configuration for syringes and other pumping mechanisms used in medical injection procedures Several representative embodiments of the present invention in which light energy is used in connection with syringe encoders are discussed below.

In the case that light energy is propagated through a length of material in which indicator(s) are formed in the present invention, one can, for example, take advantage of the properties of light refraction/reflection at an interface between two different media to assist in efficiently propagating light through the length of the media having the higher refractive index. These different media can, for example, be a translucent or transparent syringe wall and the air surrounding the syringe wall.

Figure 2A:
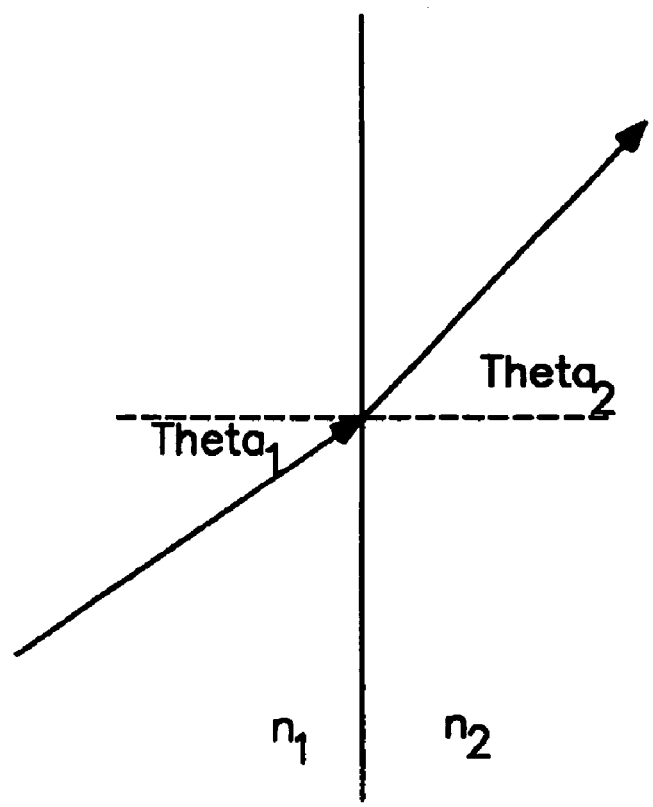
FIG. 2A illustrates the behavior of light energy incident upon an interface between two media having different refractive indices as provided by Snell's law.

The refraction of light at an interface between two dielectric media is governed by Snell's Law as follows:

$$n_1 \sin\theta_1 = n_2 \sin\theta_2$$

wherein $n_1$ and $n_2$ are the refractive indices of each dielectric material and $\theta$ or Theta is the angle of incidence of the light (as measured with respect to an orientation or plane normal to the interface). Snell's law is represented graphically in FIG. 2A.

Figure 2B:
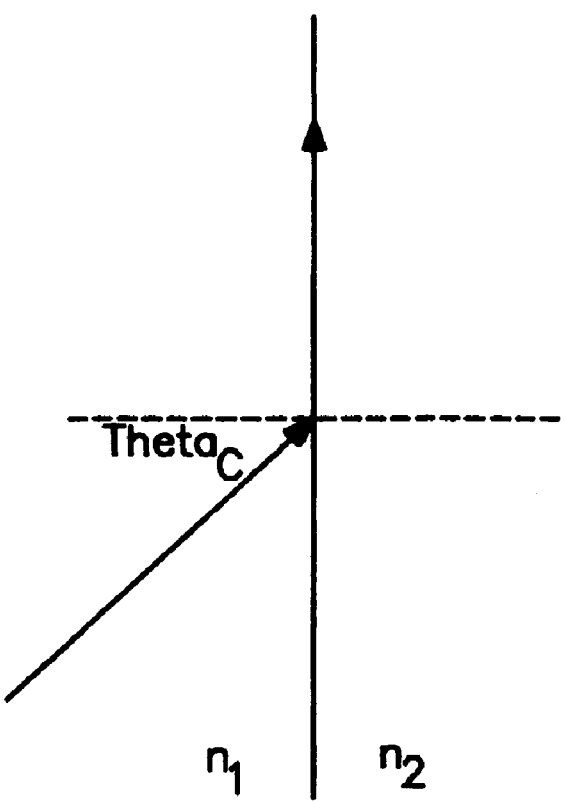
FIG. 2B illustrates the behavior of light incident upon an interface at a critical angle to result in theoretically total internal reflectance.

In the special case where light is initially traveling in a material with a higher index of refraction, and then encounters a region of lower index of refraction, the potential for the light to be reflected (internally within the first material) at the interface boundary arises. A critical angle can be defined in the following manner: any light that encounters the dielectric interface at an angle less than the critical angle will not be reflected at the interface—it will proceed on into the second medium. In other words, the angle of refraction at the critical angle is 90°. Mathematically, the critical angle is given by $$n_1 \sin\theta_1 = n_2$$
$$\theta_c = \sin^{-1}\left(\frac{n_2}{n_1}\right)$$

where $n_1$ and $n_2$ are the refractive indices of each dielectric material and $\theta_c$ or Theta$_c$ is the critical angle of incidence of the light. The critical angle of incidence is illustrated graphically in FIG. 2B.

Figure 2C:
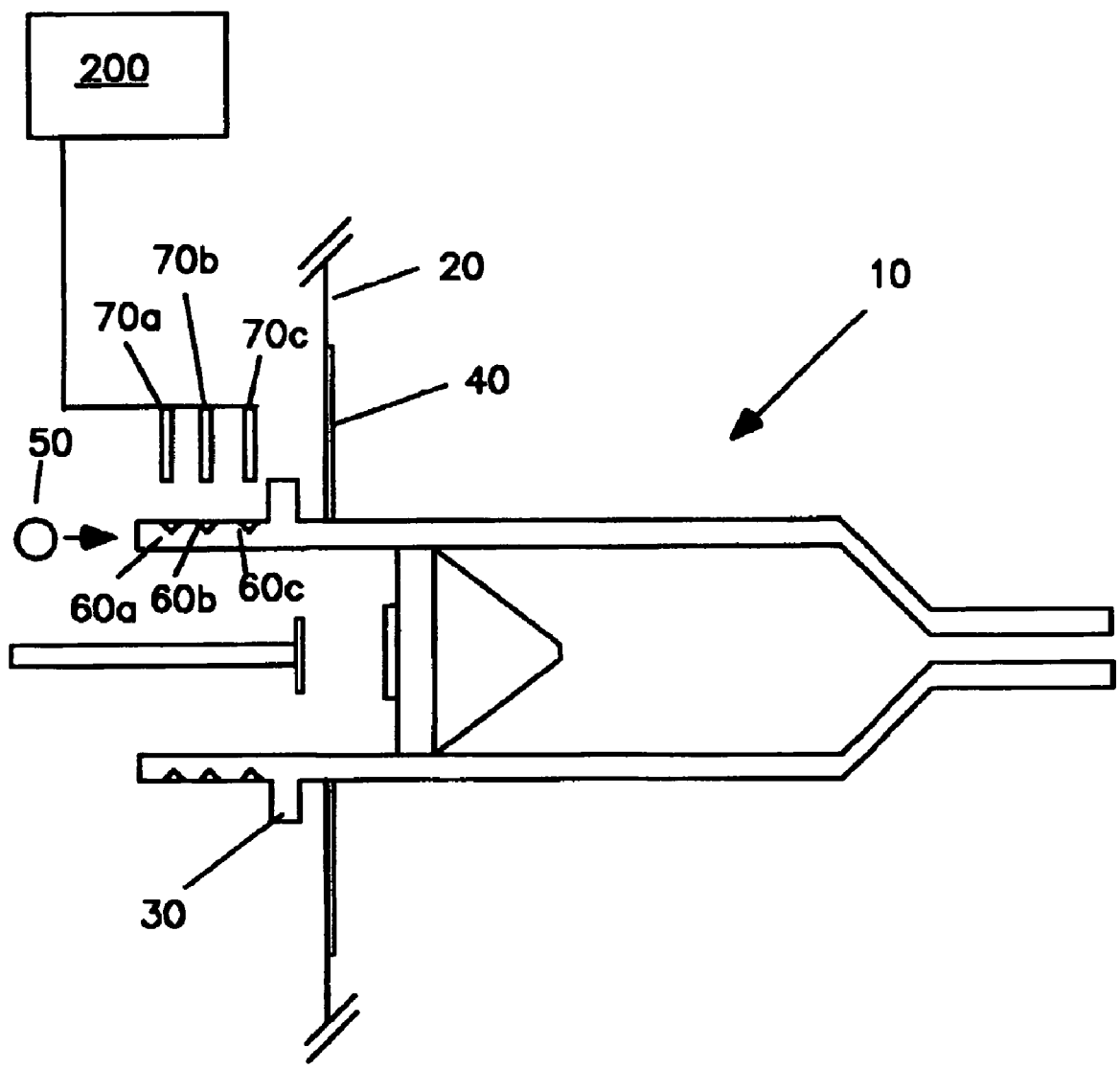
FIG. 2C illustrates a side cross-sectional view of an embodiment of a syringe encoding system of the present invention.

FIG. 2C illustrates a syringe 10 having at least a portion thereof formed from a generally translucent or transparent material such as glass or a clear plastic. Syringe 10 can, for example, be removably positioned upon a powered injector 20 by the interaction of syringe flange(s) 30 and drip flange 40 as with mounting means on and/or in the front wall of injector 20 as described, for example, in U.S. Pat. No. 5,997,502. A light source 50 is, for example, positioned within injector 20 to transmit or propagate light energy in a generally axial direction (that is, parallel to the axis of syringe 10) through the wall of syringe 10. The light energy can be outside the wavelength of visible light to reduce interference from ambient light. Light source 50 can also be pulsed to improve detectability.

Figure 2D:
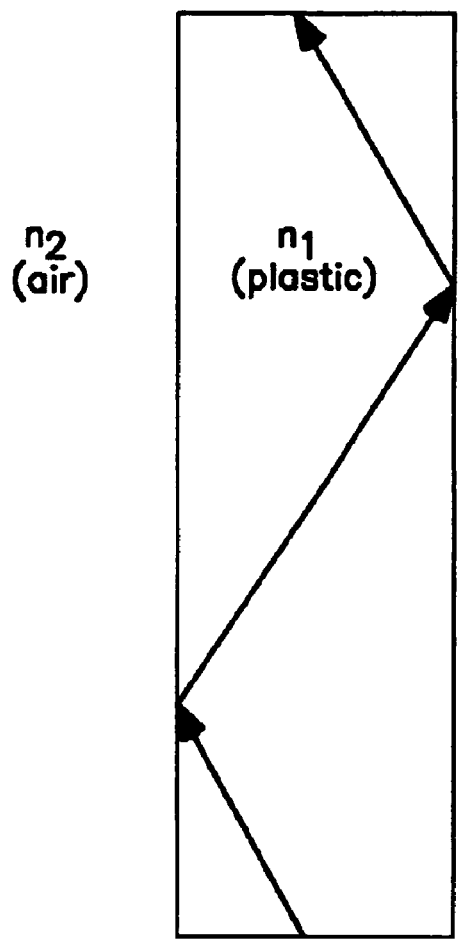
FIG. 2D illustrates total internal reflectance of light within the syringe wall material.

FIG. 2D illustrates light being internally reflected within the syringe wall. In general, all light striking the interface between the syringe wall and the air at an angle greater that the critical angle (as measured from a vertical plane in the orientation of FIG. 2C or as measured from a horizontal planed in the orientation of FIG. 2D-*that* is, a plane normal to the syringe-air interface) will be internally reflected within the syringe wall and propagate therethough in a generally axial direction.

In one embodiment, syringe 10 was manufactured from polyethylene terephthalate (PET), for which the index of refraction measured at 632.8 nm (Helium-Neon laser output) is approximately 1.68 for an ambient temperature of 21° C. Given a refractive index of approximately 1.00 for air, this material resulted in a critical angle for the air-syringe interface of approximately 37° degrees. Therefore, if the light hits the interface at an angle greater than this value, it will be internally reflected. In the case of no scattering or absorption, this reflection is theoretically perfect. Indeed, measurements have shown that the reflection coefficient from a dielectric interface within, for example, a high quality optical fiber exceeds 0.9999. See, for example, *Handbook of Optics*, McGraw-Hill, p. 13-6. In practice, the reflection coefficient will decrease as imperfections in the material increase.

Given the approximately 37° critical angle for the syringe-air interface, light being internally reflected within the plastic of the syringe wall is striking the interface at angles greater than or equal to the critical angle. Light that strikes the interface at a numerically "shallower" or smaller value will be transmitted through the interface out into the air.

Figure 2E:
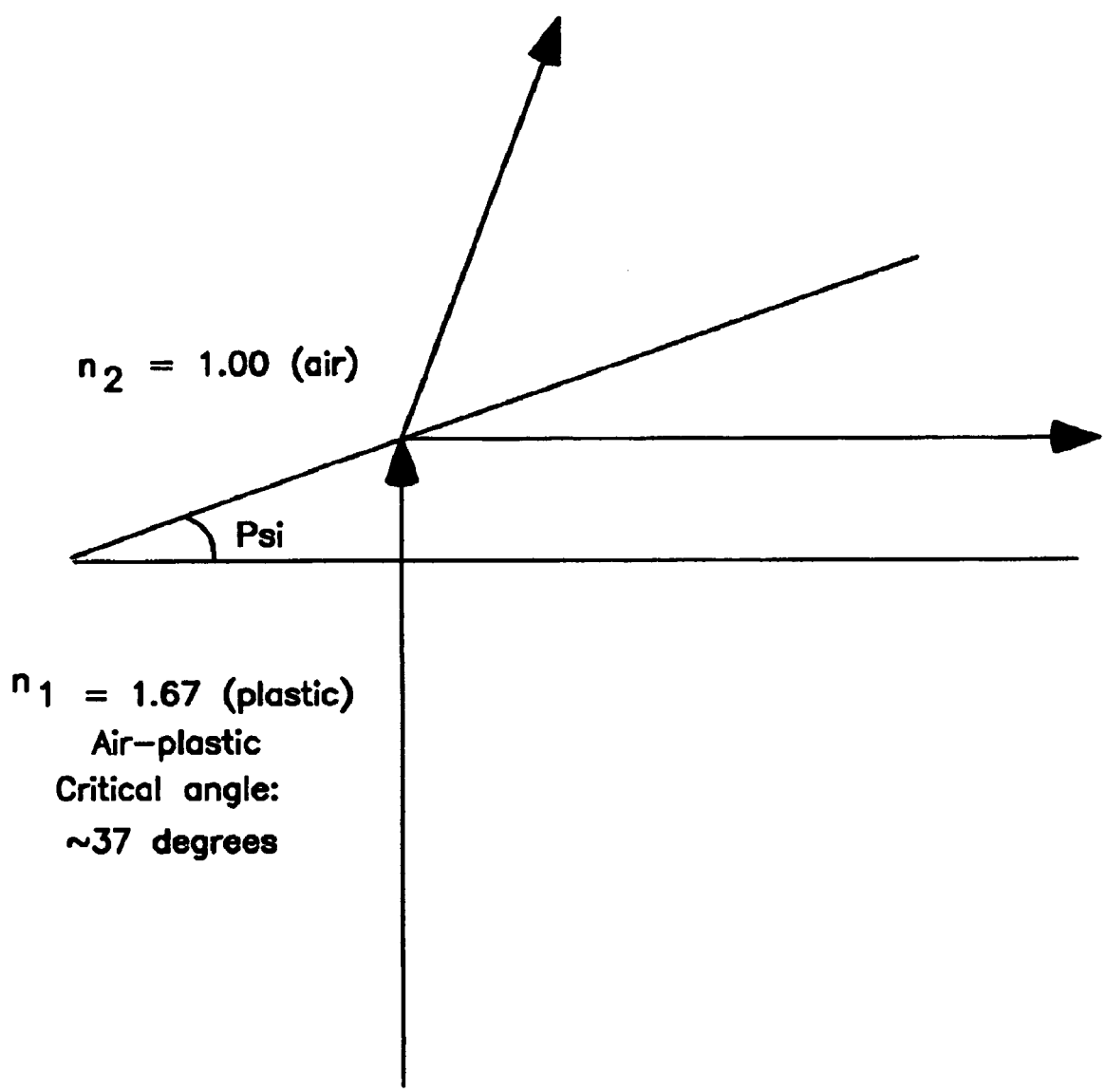
FIG. 2E illustrates the use of angled surfaces within the syringe to transmit light outside the syringe wall at a predetermined location.

FIG. 2E illustrates the case of light vertically propagating within the syringe wall encountering a beveled or angle interface. Not all of the light is reflected at the angled interface. In the case of LED emissions, for example, the light output is typically Gaussian with additional "misdirection" of the photons occurring as the light is scattered within the plastic. The net result is a packet, or cone, of light that is propagating within the plastic. When this cone of light strikes the angled interface, some of the light will continue through the interface into the air. In FIG. 2E, if the angle Psi exceeds the critical angle (37°), light will be reflected from the interface. If that light then encounters another angled interface, some of the light will be directed back into the plastic where it will again propagate until it hits the next angled interface. This scenario provides a slight increase in the total amount of light being redirected within the syringe wall (that is, to the right in the orientation of FIG. 2E) while also spatially distributing the light. The number of angled interfaces (for example, grooves, notches or raised features) that provides optimum light redirection can be readily calculated given the material properties, the angle(s) of the angled interfaces and nature of the light source.

In FIG. 2C, syringe 10 includes a series of indicators that are formed as angled surfaces or notches 60a-60c. The angled surfaces or indicator notches 60a-60c act as portals to transmit a portion of the light being propagated through the syringe wall into the surrounding air. Light sensors 70a-70c are positioned adjacent notches 60a-60c, respectively. The presence or absence of one or more of notches 60a-60c (or the relative positions of notches 60a-60c with respect to each other) can, for example, represent a binary or other code that corresponds to a particular syringe configuration (for example, a certain volume syringe containing a certain concentration of a particular type of contrast medium) as, for example, interpreted by a processing unit 200 in communicative connection with sensors 70a-70c. Notches 60a-60c can be placed relatively close to light source 50 to ensure that the amount of light transmitted into the surrounding air is measurable. In that regard, the total light energy available for measurement will decrease as the distance from light source 50 increases (for example, via scattering, absorption and/or transmission through angled surfaces 60a-60c). Notches 60a-60c can be formed around the circumference of syringe 10. In this manner, the orientation of syringe 10 (that is, the degree of rotation about its axis) is irrelevant to the ability of sensors 70a-70c to measure light transmitted from syringe 10.

The ability to (1) position indicators (for example, indicators 60a-60c of FIG. 2C) in general alignment parallel to the axial orientation of syringe 10, and (2) propagate energy from source 50 through the syringe wall generally parallel to the axis of syringe 10 provides substantial space for multiple indicators along the length of syringe 10 and reduces or eliminates problems in propagating energy that can arise from the curvature of the syringe wall around the axis of syringe 10. Moreover, this orientation facilitates positioning of energy source 50 and sensors 70a-70c with only minor changes in existing syringe and injector designs.

Figure 2F:
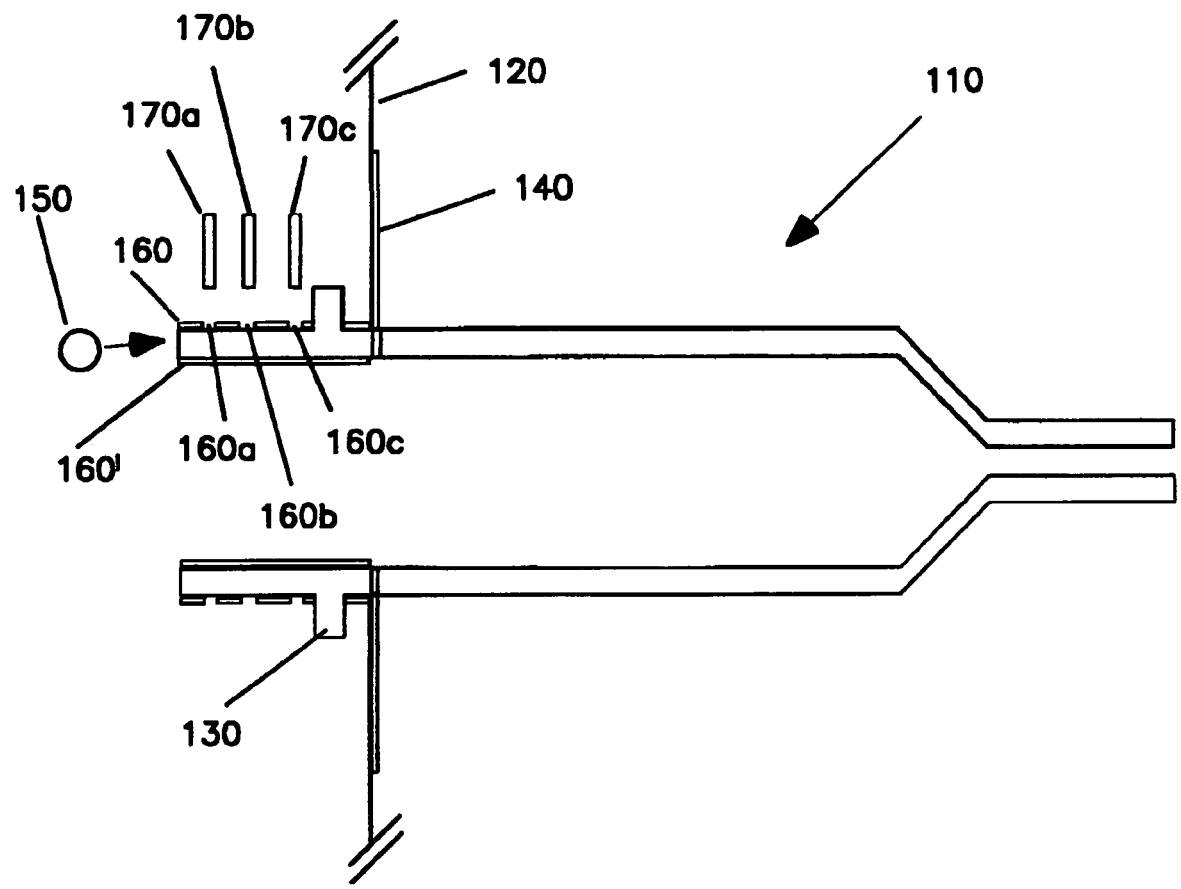
FIG. 2F illustrates a side cross-sectional view of another embodiment of a syringe encoding system of the present invention.

FIG. 2F illustrates an alternative embodiment of a syringe 110 attached to a powered injector 120. As discussed above, syringe 110 includes a mounting flange 130 and a drip flange 140. Injector 120 includes a light source 150 positioned to transmit light into the syringe wall so that light propagates through the syringe wall in a generally axial direction. In this embodiment, at least the rearward section of syringe 110 includes a shield or barrier 160 that is placed at least on the exterior perimeter of syringe 110. Shield 160 includes several indicators formed as openings or portals 160a-c that allow light to be transmitted into the surrounding air whereas the remainder of shield 160 prevents light from being transmitted therethrough. Such light transmitted into the surrounding air can be detected by sensors 170a-170c as discussed above to provide information regarding the syringe configuration. A shield 160' can also be provided on the interior diameter of the syringe wall. Shields 160 and 160' can, for example, be an opaque plastic or an opaque ink. Shields 160 and 160' can also be reflective to ensure that light is propagated axially in an efficient manner.

Although internal reflectance arising from materials of different refractive indices as described above is useful in efficiently propagating light energy through the length of a medium, internal reflectance is not necessary in practicing the present invention. For example, reflective shields or linings as described in connection with FIG. 2F can be used to propagate light energy through a length of material. Moreover, those light rays propagating through a length of material generally parallel to the axis of the length of material (without internal reflection) can interact with indicators of the present invention in a detectable manner.

In several embodiments of the present invention, steps are preferably taken to prevent interference from background or ambient light (that is, light not originating from the light source(s)). For example, narrow bandwidth detection can be used in which the light source(s) and sensor(s) operate over a very narrow range of optical wavelengths. Moreover, synchronous detection can be used in which the light source(s) are modulated at some frequency and the sensor electronics are selectively sensitive to signals varying at that frequency. At the simplest level, the difference in detected signal between a source on state and a source off state is measured. Many other detection schemes as known, for example, in the optical detection arts are suitable for use in the present invention.

In the embodiments of FIGS. 2C and 2F, all indicators for directing/transmitting light to sensors are located in or on the syringe wall, to the rear of drip flanges 40 and 140. As clear to those skilled in the art, such indicator/sensor pairing can be located anywhere along the syringe wall. Moreover, the syringe can include a portion or member that is separate from the syringe wall through which energy can be transmitted for syringe information encoding.

FIGS. 3A-3E illustrate several further embodiments of the present invention. Each of FIGS. 3A-3E illustrates a length of material through which electromagnetic energy (for example, light energy) can pass or propagate. The length of material can for example be a portion of a syringe wall, a portion of a syringe adapter or a portion of a syringe or other encoder that is, for example, associated with and/or attachable to syringe, a syringe adapter (for example, a sleeve that is positioned adjacent to or that fits over a syringe or a syringe adapter) or another device to be encoded. Examples of adapters suitable for use in the present invention are disclosed, for example, in U.S. patent application Ser. No. 09/365,285, filed on Jul. 30, 1999, and in U.S. patent application Ser. No. 09/633,299, filed on Aug. 8, 2000, assigned to the assignee of the present invention, the disclosures of which are incorporated herein by reference. In general, adapters enable use of syringes not specifically designed for use with a particular injector.

Figure 3A:
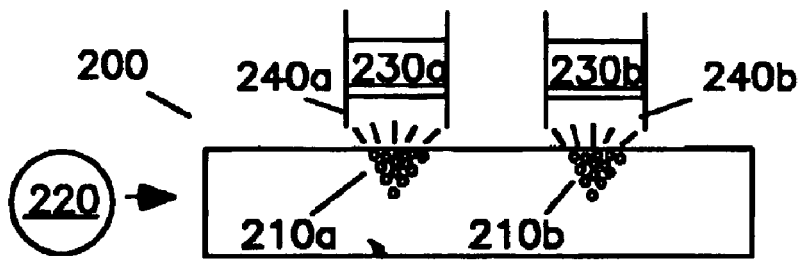
FIG. 3A illustrates a side cross-sectional view of an embodiment of a syringe encoder in which an indicator scatters light to be detected by corresponding sensor.

The lengths of material of FIGS. 3A-3E are referred to simply as syringe encoders below. In FIG. 3A, syringe encoder 200 includes indicators 210a and 210b that are discontinuities in syringe encoder 200 that act to transmit/redirect/scatter light propagating through syringe encoder 200 from light source 220. Such discontinuities can, for example, be formed as irregularities within the material of syringe encoder 200 or by incorporating another material within syringe encoder 200 (such as by coextrusion of polymeric materials). Light transmitted/redirected/scattered from indicators 210a and 210b is detected by sensors 230a and 230b, respectively. In the embodiment of FIG. 3A, sensors 230a and 230b are surrounded by shields or columnators 240a and 240b, respectively. Shields 240a and 240b extend toward the surface of syringe encoder 200 to reduce or prevent light transmitted/redirected/scattered from indicator 220b from being detected by sensor 230a and to prevent light transmitted/redirected/scattered from indicator 220a from being detected by sensor 230b, respectively (sometimes referred to as "crosstalk").

Figure 3B:
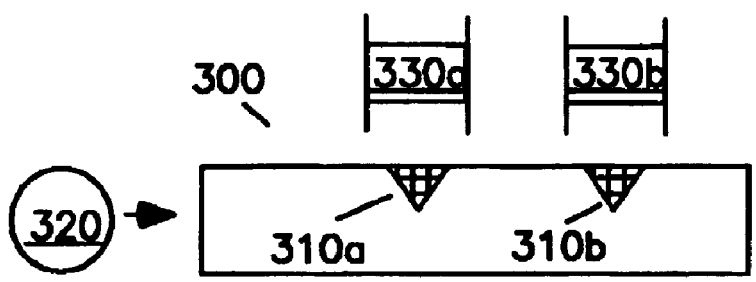
FIG. 3B illustrates a side cross-sectional view of an embodiment of a syringe encoder in which an indicator absorbs light.

In FIG. 3B, syringe encoder 300 includes indicators 310a and 310b that absorb light energy propagated through syringe encoder 300 from light source 320 that would otherwise be transmitted outside of syringe encoder 300. Sensors 330a and 330b detect the presence or absence of indicators 310a and 310b as described above. In this embodiment, however, the presence of an indicator at a predetermined position results in the absence of a signal at that position. Whereas indicators 210a and 210b of syringe encoder 200 may, for example, correspond to a binary code of 11, indicators 310a and 310b of syringe encoder 300 may correspond to a binary code of 00.

Figure 3C:
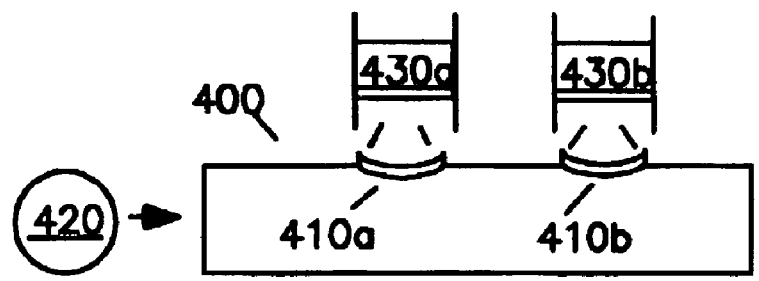
FIG. 3C illustrates a side cross-sectional view of an embodiment of a syringe encoder in which an indicator acts as a lens to focus light upon a corresponding sensor.

Syringe encoder 400 of FIG. 3C includes indicators 410a and 410b that act as lenses to focus light being propagated through syringe encoder 400 from light source 420 on sensors 430a and 430b, respectively.

Figure 3D:
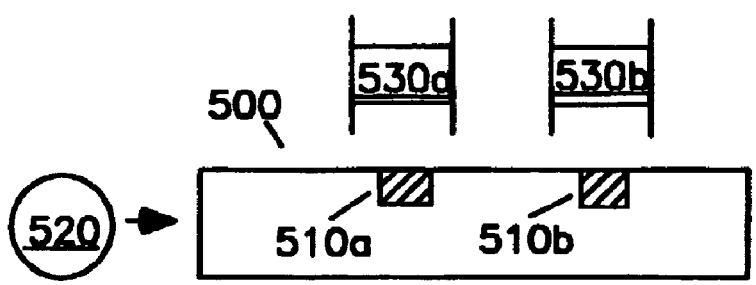
FIG. 3D illustrates a side cross-sectional view of an embodiment of a syringe encoder in which an indicator enters into an "excited" state detectable by a corresponding sensor when the indicator is contacted by electromagnetic energy.
Figure 3E:
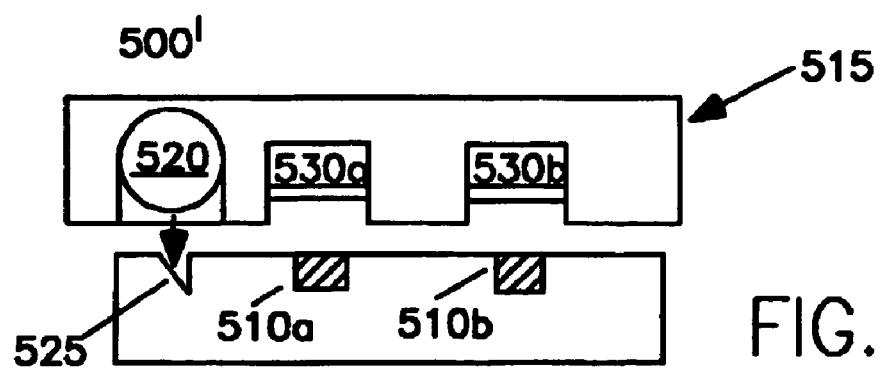
FIG. 3E illustrates a side cross-sectional view of another embodiment of the syringe encoder of FIG. 3D in which a source of light energy is placed in generally the same plane as the sensors thereof.

Syringe encoder 500 of FIG. 3D includes indicators 510a and 510b that are placed in an xcited state when light from light source 520 impinges thereupon. For example, indicators 510a and 510b can include a material that fluoresces when light energy impinges thereupon. The excited state (for example, fluorescence) of indicators 510a and 510b is detectable by sensors 530a and 530b, respectively. Syringe encoder 500' of FIG. 3E is similar in operation to that of syringe encoder 500. However, in the embodiment of syringe encoder 500', light source 520 is placed in generally the same plane as sensors 530a and 530b. Light from light source 520 is redirected to propagate through syringe encoder 500' by angled surface 525. Moreover, in the embodiment of FIG. 3E, light source 520 and sensors 530a and 530b are incorporated in a carrier 515, which can, for example, be a cylindrical sheath such as a syringe heater as known in the art.

Figure 4:
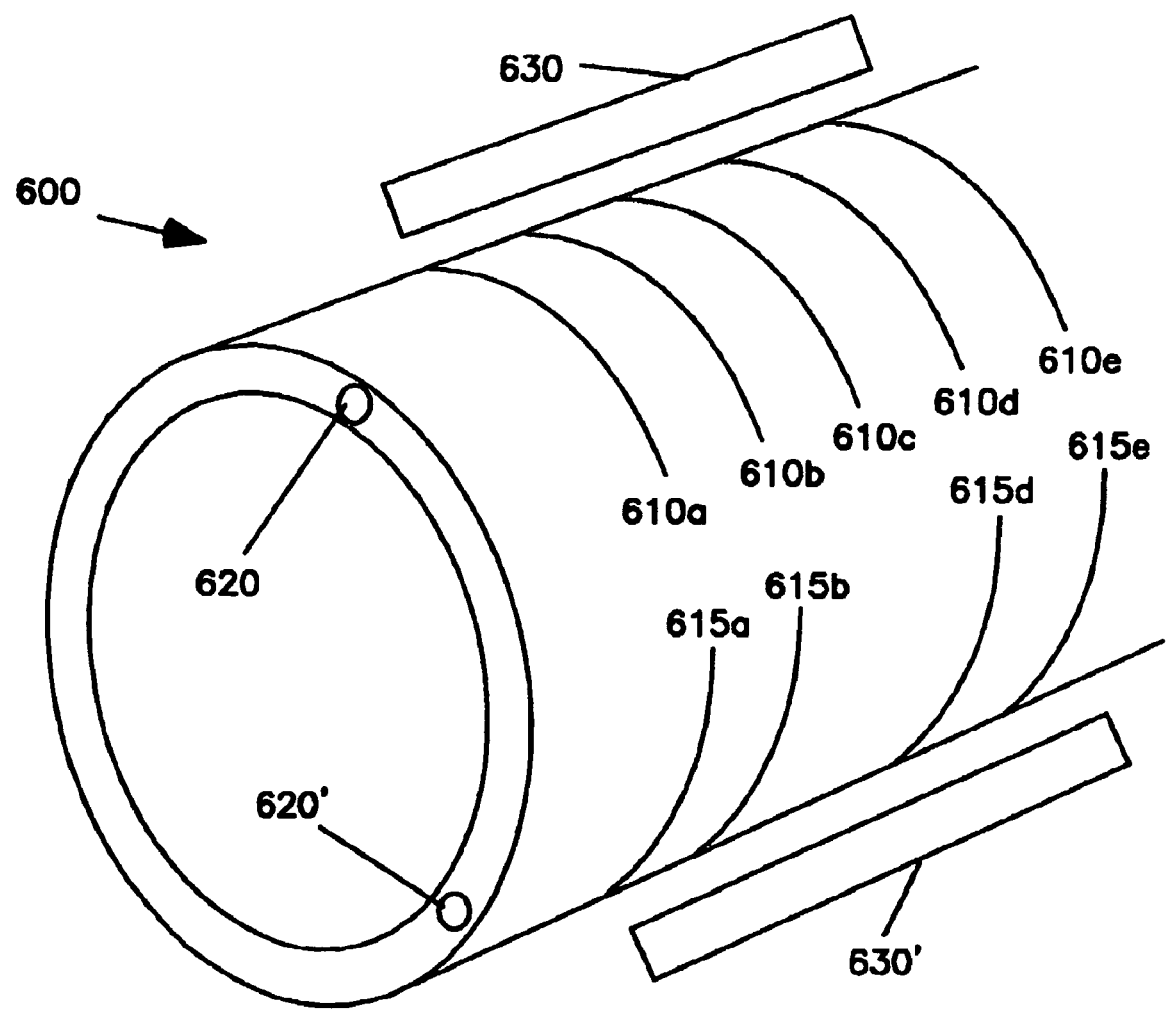
FIG. 4 illustrates a rear perspective view of an embodiment of a syringe encoder including two sets of indicators positioned on different quadrants of the syringe encoder.

As discussed above, the indicators of the present invention can for example extend around the circumference of a syringe or a syringe adapter to a sufficient extent so that the orientation of the syringe, the syringe adapter or the syringe encoder (that is, the degree of rotation about its axis) with respect to the injector, light source and/or sensor bank is irrelevant to the ability of the corresponding sensors to measure how the indicators modify energy propagated through the syringe, the syringe adapter or the syringe encoder. However, orientation can be used to encode more information. FIG. 4, for example, illustrates a syringe encoder 600 including a plurality (two in this embodiment) of sets of indicators to set forth a plurality of binary codes. Indicators 610a, 610b, 610c, 610d and 610e (the first set) and indicators 615a, 615b, 615d and 615e (the second set) are positioned, for example, in different sections or quadrants of generally cylindrical syringe encoder 600. Syringe encoder 600 further includes two light sources 620 and 620' as well as two sensor banks 630 and 630'. Encoder 600 can, for example, be a portion of a syringe wall or a portion of a syringe adapter. Likewise, encoder 600 can be attachable to a syringe or a syringe adapter.

In the embodiment of FIG. 4, at least one indicator in each set of indicators, for example, the last indicator in each set of indicators (that is, indicators 610e and 615e) can be used to determine if a syringe is properly attached to and/or properly positioned with respect to a powered injector (not shown in FIG. 4). Indicators 610e and 615e (and/or other indicators) can also be used to check parity and/or to calibrate the sensitivity of sensors 630 and 630', which can, for example, be an array of sensors or a single sensor such as a charge-coupled device (CCD) camera. For example, the indicators of FIG. 4 may be angled notches as discussed in connection with the embodiment of FIG. 2C. The amount of light sensed by sensor banks 630 and 630' as a result of indicators 610e and 615e, respectively, can provide information for calibrating sensitivity settings for determining whether other indicators are present or absent at various positions on syringe encoder 600.

Dedicating the use of indicators 610e and 615e as position and/or calibration indicators, the presence or absence of other indicators can be used to set forth binary code(s) of predetermined lengths. In FIG. 4, two binary codes of four bits each are represented by indicators 610a, 610b, 610c and 610d of the first set of indicators and by indicators 615a, 615b and 615d of the second set of indicators. The binary code of the first set of indicators is 1111, while the binary code of the second set of indicators is 1101 (an indicator at the third or "c" position is absent in the second set of indicators). The two binary codes correspond to a particular syringe configuration as can be provided, for example, in a look-up table stored in computer memory. With the use of a sensor or sensors having a relatively wide detection range (for example, a CCD camera) the absolute position of a set of indicators representing a binary code is not as important as the case in which sensors having a relatively narrow range of detection are used, requiring general alignment of an indicator/sensor pairing.

Figure 5A:
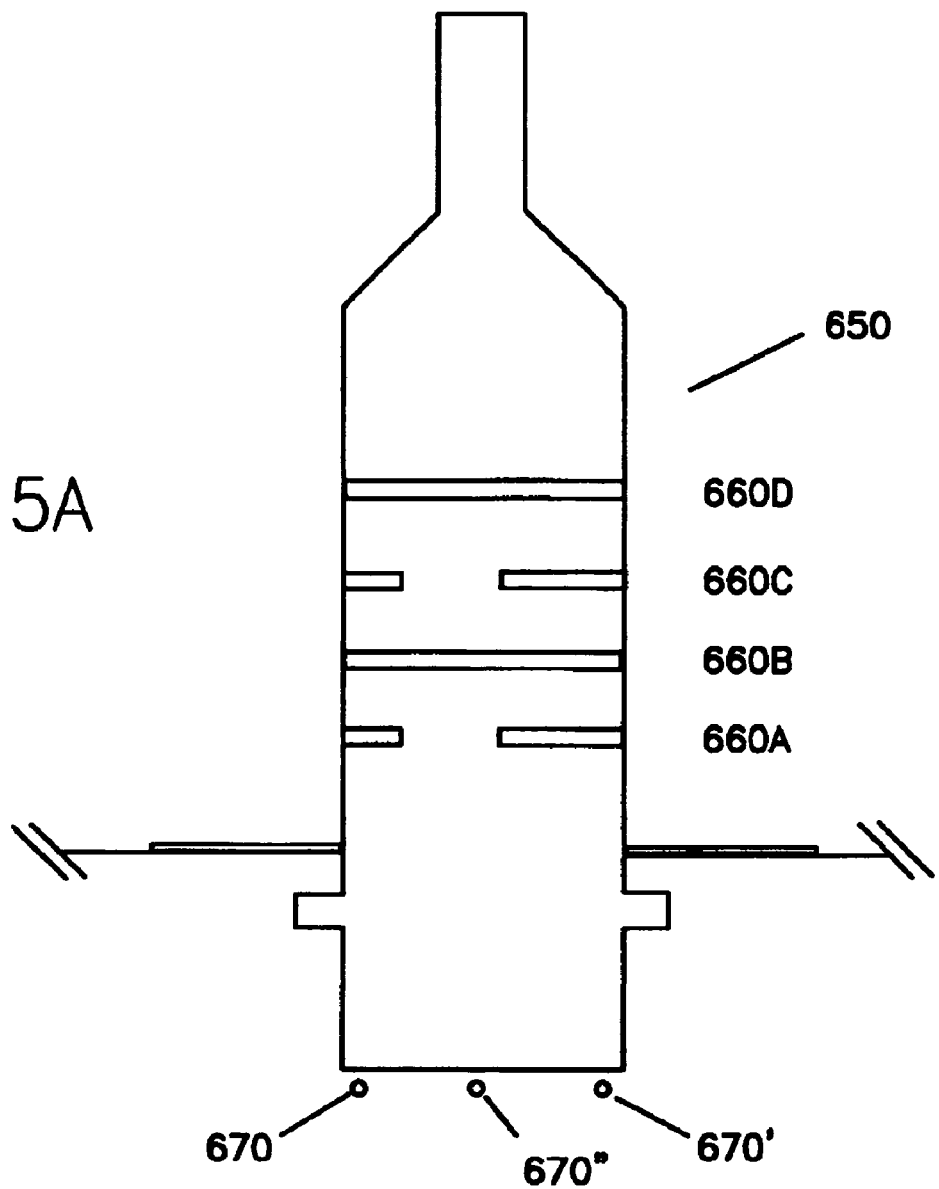
FIG. 5A illustrates a side view of an embodiment of a syringe including multiple sets of indicators.
Figure 5B:
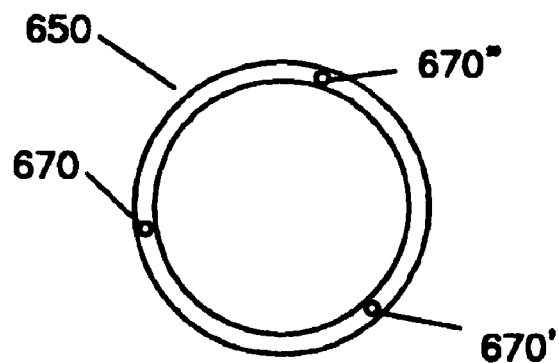
FIG. 5B illustrates a bottom view of the syringe of FIG. 5A.

FIGS. 5A and 5B illustrate another embodiment of the present invention (similar to that of FIG. 4) in which several bands of indicators 660A, 660B, 660C and 660D extend at least partially around the circumference of a syringe 650 at predetermined positions along the length of syringe 650. As illustrated in FIG. 5B, three energy sources 670, 670' and 670" are positioned at different positions around the circumference of syringe 650 adjacent the rearward end of syringe 650. Four detectors (not shown in FIGS. 5A and 5B) can be placed in general angular alignment (i.e., about the circumference of syringe 650) with sources 670, 670' and 670" at each band level of indicators (4 bands×3 sources=twelve total detectors). Dedicating, for example, the D-band of indicators to position and/or calibration determinations as described above, one is left with three binary codes of three bits each or 216 possible different encoded configurations.

In FIG. 6, a syringe encoder 700 includes indicators 710a and 710c that are angled surfaces formed in the surface of syringe encoder 700. Three energy sources 720, 722, 724 are pulsed sequentially as shown in the timing diagram of FIG. 6 as waveforms S720, S722, S724. S720 and S724 are positioned over indicators or grooves 710a and 710c, respectively, in the syringe barrel, which transmit light to a receiver 730. In the embodiment of FIG. 6, there is no indicator on the syringe corresponding to the fixed position of energy source 722. No energy is, therefore, transmitted to receiver 730 when S722 is pulsed on. Consequently, the reception portion R of the timing diagram shows pulses received from S720 and S724 but not from S722. The presence or absence of indicators at each source can represent a digital code as described above.

Figure 7:
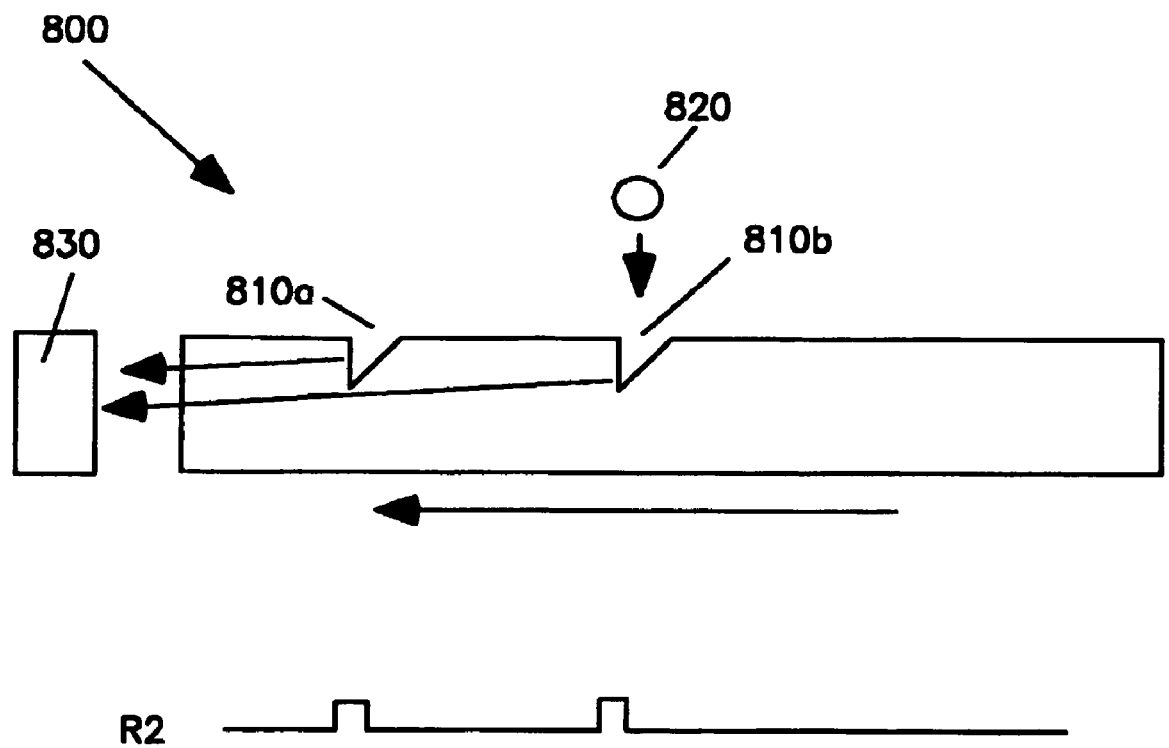
FIG. 7 illustrates a side cross-sectional view of a syringe encoding system in which syringe configuration is determined in a dynamic fashion.

In the above discussion, syringe configuration information is read in a static fashion. Syringe configuration information can also be read in a dynamic fashion using the syringe encoding systems of the present invention. As syringe encoder 800 is moved to the left in the orientation of FIG. 7 (for example, as a syringe is attached to a powered injector), indicators 810a and 810b redirect at least a portion of light energy from light source 720 through syringe encoder 800 to a receiver 830 as illustrated with arrows in FIG. 7. A received signal R2 provides information on syringe configuration.

Figure 8:
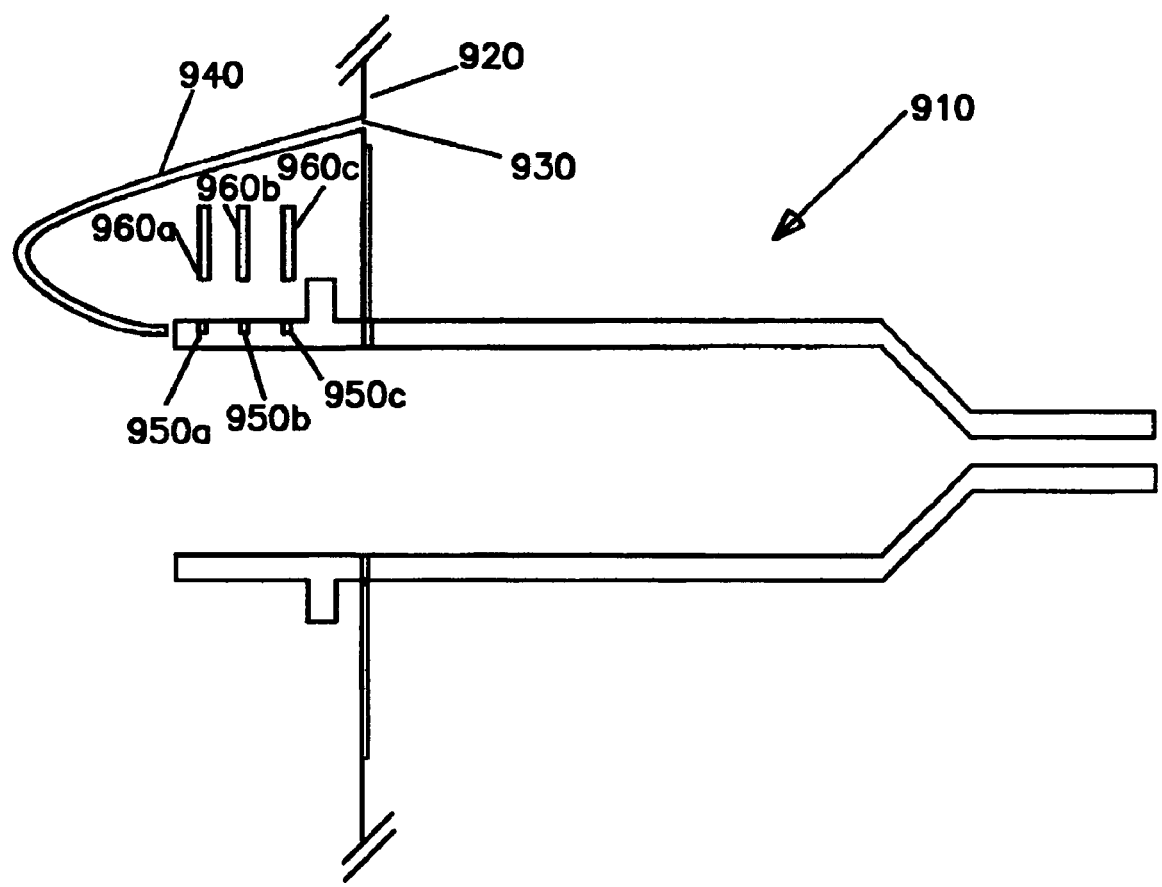
FIG. 8 illustrates side cross-sectional view of a syringe using ambient light as a light source for syringe encoding.

In the case that light energy is used in the present invention, the light source can be a powered light source such as a light emitting diode or LED or other powered light source as know in the art. However, ambient light can also be used. In FIG. 8, for example, a syringe 910 is attached to a powered injector 920. Powered injector 920 includes an opening 930 through which ambient light can pass. Opening 930 is in communicative connection with, for example, a fiber optic cable 940. Fiber optic cable 940 terminates adjacent a rearward end of syringe 910 and provides light energy to one or more indicators 950a, 950b and 950c. As discussed above, detectors 960a, 960b and 960c are adapted to sense modification of the light energy by indicators 950a, 950b and 950c, respectively.

In the case that the indicators of the present invention use refraction and/or reflection to direct light energy to corresponding detectors, the design (for example, position, depth and angle) of the indicators can have substantial effect on the light detected by the detectors. To study these and other effects in several designs of the present invention, a ray-tracing model was constructed using Mathcad software, available from MathSoft of Cambridge, Mass. In this software, the intensity of reflected or refracted rays is varied with the angle of incidence according to Fresnel's laws.

In the models, the syringe or encoder was assumed to be rotationally symmetric and its cross-section was described by a closed polygon. The syringe material was assumed to be optically uniform and isotropic, with a refractive index of 1.68. A nominal value of 3 dB per inch was used for optical attenuation within the syringe material.

A point light source was used with a Gaussian beam profile. The source was placed 0.2 inches from the rear/bottom edge of the syringe and a half-power beam half-angle of 5° was used. To test each design, about 500 rays from the source were traced.

Each ray was traced to its first point of incidence, and the attenuation over that distance was taken into account. The transmitted and reflected rays were calculated according to Fresnel's laws. The transmitted and reflected rays were then independently traced, each yielding new transmitted and reflected rays at their next incidence. This iterative process quickly generated many rays from the first ray. A ray was terminated when it either finally exited the syringe or its intensity dropped below a threshold value. The rays that exited the syringe were collected on an imaging surface, which was a cylinder placed around the syringe at a radius corresponding to a likely position of sensors as described above. The point and angle of incidence were recorded, as well as the intensity of the ray.

In addition to the assumptions or conditions stated above, the model ignored the following effects or conditions: the presence of a piston head at the inside wall of the syringe; the presence of any contrast medium in the syringe cavity; and surface roughness of the syringe.

Two forms of graphical output were generated. First, all of the rays generated by a single ray were superimposed on a three-dimensional plot of the syringe. This output facilitated debugging of the code and was useful in tracking down undesirable features of particular designs. Second, a surface plot of light intensity on the image plane was generated. As an option, one can choose only those rays that hit the image plane within a certain angle of incidence to contribute to the plotted intensity. This output illustrates the overall performance of a design.

Figure 9:
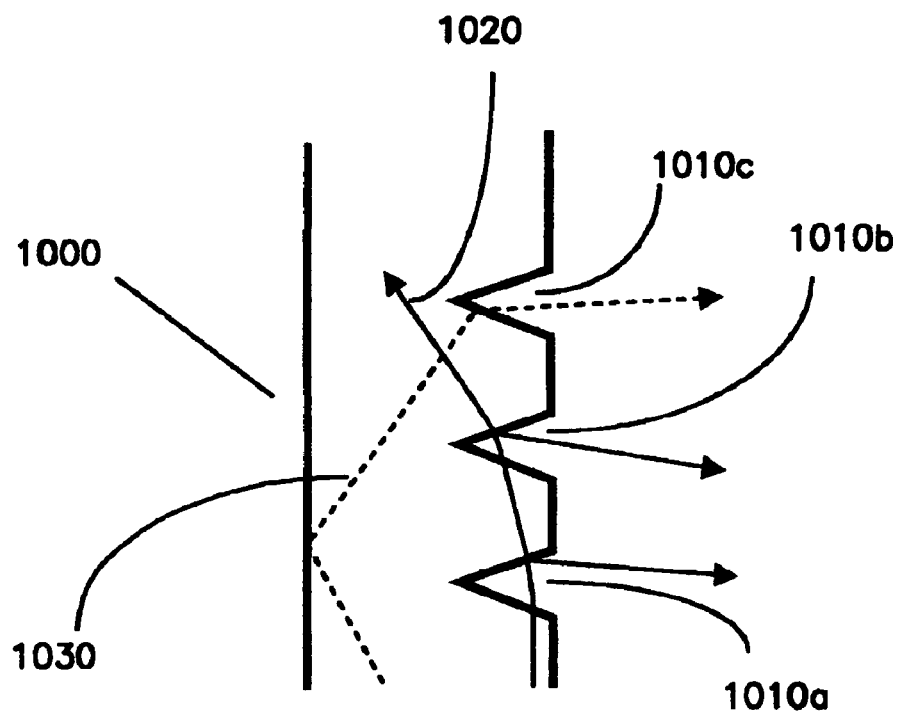
FIG. 9 illustrates a model study of a syringe encoder with angled notches.

FIG. 9 illustrates, for example, a portion of a syringe or an encoder 1000 in which the indicators are V-shaped notches 1010a, 1010b and 1010c. In FIG. 9, a light source (not shown) is positioned at the bottom of syringe 1000. In this embodiment, it is difficult to make notches 1010a, 1010b and 1010c perform independently of each other, (that is, light from one notch depends on the presence or absence of the notches preceding it or below it in the orientation of FIG. 9). In that regard, the section of the syringe wall between two notches resembles generally a prism. When light traveling generally parallel to the syringe wall passes through this prism it is bent off-axis, away from the notches above it. For example, a refracted ray 1020 is bent away from notch 1010c in FIG. 9, when passing through the syringe wall between notches 1010b and 1010c. The illumination of notch 1010c above the prism of the syringe wall in this case must rely on rays internally reflecting off the inside surface of syringe 1000. In that regard, another ray 1030 is shown to internally reflect within the syringe wall to contact notch 1010c. In the embodiment of FIG. 9, it is difficult to ensure that internally reflected rays that exit a notch by refraction and rays traveling through the notches that exit by reflection leave a notch at similar angles. This result can easily lead to cross talk between detector-indicator pairs, wherein the light from one notch reaches more than one detector as discussed above. As also discussed above, the use of columnators can reduce the effects of this problem.

However, the interdependence between the V-shaped notches makes it complicated to choose a notch shape that works well for all the notch codes. Moreover, the use of refraction also makes the design sensitive to the refractive index of the material.

Figure 10:
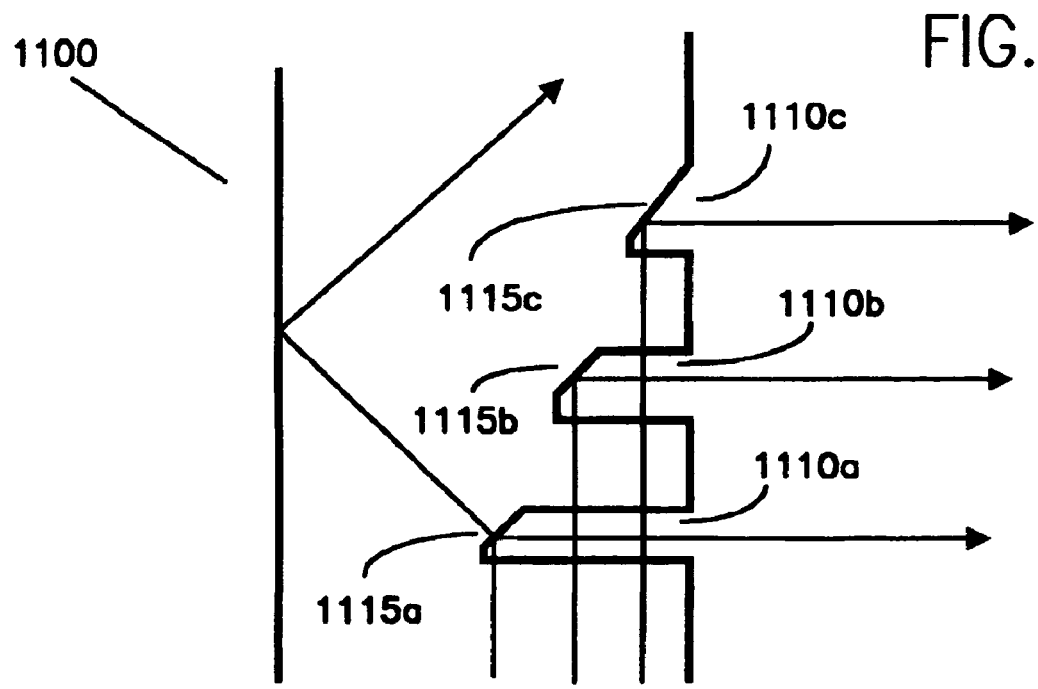
FIG. 10 illustrates a model study of a syringe encoder with reflective surfaces.

These problems can be substantially eliminated by using transmission of energy at near normal incidence to an indicator surface and reflection as illustrated in FIG. 10. Syringe 1100 includes three indicator notches 1110a, 1110b and 1110c. Indicator notches 1110a and 1110b include two generally parallel walls and a reflecting surface or wall 1115a and 1115b, respectively, oriented at generally 45° to light rays incident thereupon, resulting in reflection of the incident light rays at an angle approximately 90° to the direction of the incident light rays. Shallower indicator notch 1015c also includes a reflecting surface 1115c that is also oriented at generally 45° to light ray incident thereupon. Reflector surfaces 1115a, 1115b and 1115c reflect light to appropriately positioned detectors (not shown in FIG. 10). 11 practice, the generally parallel walls of indicator notches 1110a and 1110b preferably have a draft angle to allow a mold tool to be released in the case of an injection-molded syringe. A small angle of approximately 2° is likely sufficient and will not significantly affect the optical properties of indicator notches 1110a and 1110b.

Because reflector surfaces 1115a, 1115b and 115c are offset or positioned at different depths within the syringe wall and reflection rather than refraction is used to transmit light from indicator notches 1110a, 1110b and 1110c to corresponding detectors, it is possible for indicator notches 1110a, 1110b and 1110c to affect the light energy generally independently of each other. Moreover, the design of FIG. 10 is substantially insensitive to the refractive index of the syringe material.

The only remaining interdependent effect between indicator notches 1110a, 1110b and 1110c is the reduction of the intensity of light energy as it is transmitted through the notch walls. Taking multiple reflections into account, the intensity of the transmitted light is reduced by about 13% (for a refractive index of 1.68) after passing through each notch. The reduction amounts to 50% after passing through four indicator notches. One can compensate for such a reduction in intensity by increasing the size of the 45° reflector surfaces of indicator notches as one proceeds further down the axis or length of syringe 1100. Accurately balancing the brightness of each indicator notch may thus involve changing the size of each reflector surface according to the particular binary code involved (that is, according to the presence or absence of the preceding indicator notches).

Figure 11:
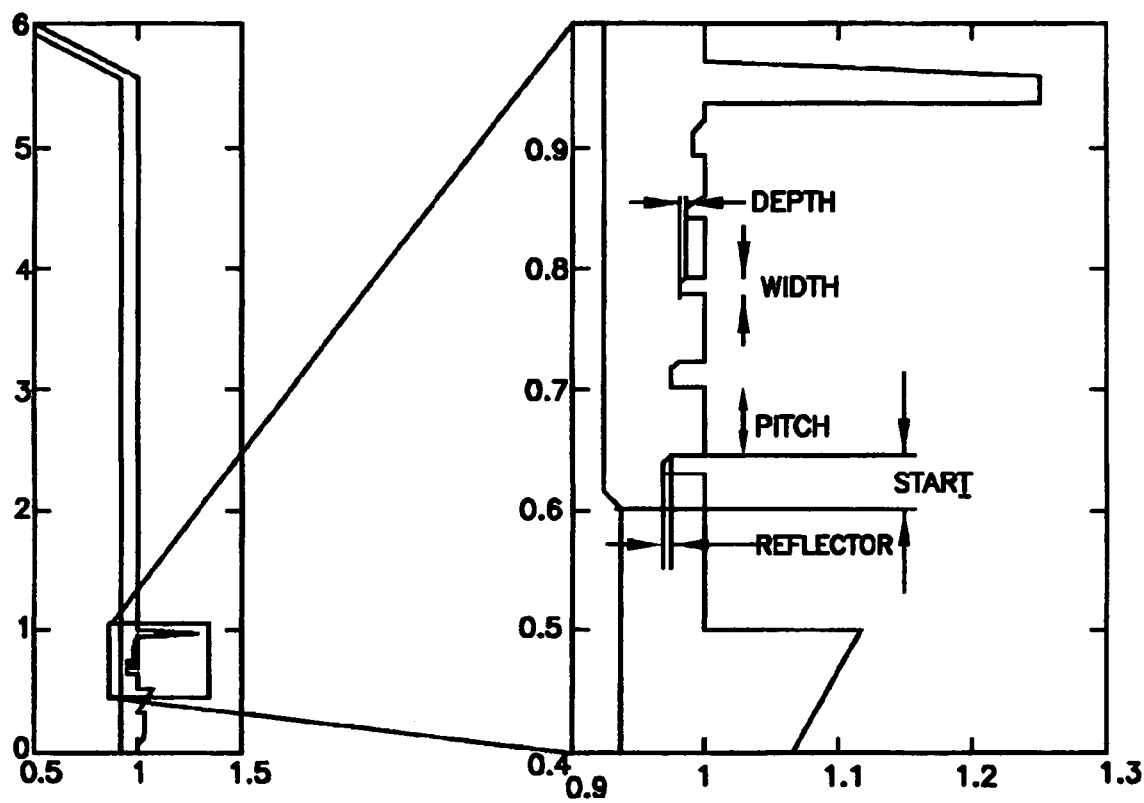
FIG. 11 illustrates dimensions of one embodiment of a model syringe design.

A representative model of the embodiment of FIG. 10 is illustrated in FIG. 11. Several preferred constraints were incorporated in the model of FIG. 11. For example, the maximum notch depth was set to half of the syringe wall thickness to maintain structural integrity. If the difference in depth between two neighboring indicator notches is less than the radial width of the reflector surface, then the reflector surface of the first notch will partially shadow the reflector surface of the second notch, reducing the amount of light reflected from the second notch. This effect is partially compensated by rays reaching the reflector surfaces via internal reflection off the outside surface of the syringe wall as shown in FIG. 10. However, a lower limit is preferably set on the increment in depth from one notch to the next. A minimum notch width of approximately 0.5 mm was set according to the thinnest section that can be used in a certain molding tool. The minimum notch width limits the size of the reflector surface, and hence the amount of light reflected from each reflector surface. Minimum spacing between notches is preferably set to eliminate cross talk. In one model, the maximum spacing possible was chosen. It is also desirable to avoid secondary reflections. In other words, it is desirable that the refracted ray from each reflector surface should not subsequently hit the reflector surfaces further down the syringe, as shown in FIG. 10. This is a more complicated geometric constraint that also involves the refractive index of the syringe.

FIG. 11 illustrates the dimensions of the model design, in which the parameters are the same for each notch, apart from depth, which had a fixed increment from one notch to the next. The selected dimensions were: (1) pitch: 0.064 in., (2) width: 0.020 in., (3) start: 0.032 in., (4) reflector surface size: 0.008 in.; and (5) depth increment: 0.008 in. The depth of the first indicator notch was set as the reflector size plus 4×(depth increment), which is approximately 0.040 in (or approximately 1 mm), or approximately half of the syringe wall thickness. The syringe wall can be thickened in the region of the indicator notches to preserve the mechanical strength of the syringe.

Figure 12:
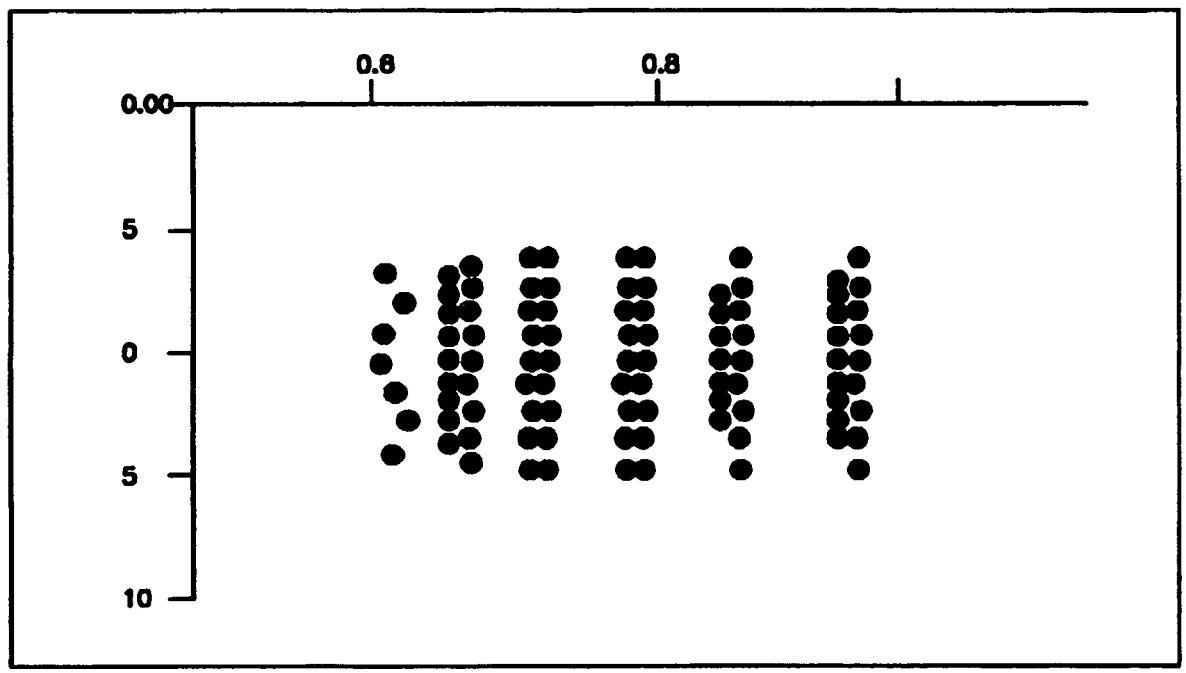
FIG. 12 illustrates the result of tracing light rays through the model syringe of FIG. 11.

In the model, a cylindrical image plane was placed at a radius of approximately 1.15 inches. FIG. 12 illustrates the result of tracing 500 rays through the syringe and shows the position of the endpoints of the rays on the cylindrical image plane, with the Z-coordinate plotted in inches on the horizontal axis and the angle around the cylinder plotted in degrees on the vertical axis.

Five main image areas can be identified, one for each indicator notch. The leftmost image area is much weaker than the image areas corresponding to the indicator notches and is a result of light scattering off a guide or positioning element at the bottom of the syringe. The light scattering off of the positioning element is incident on the image cylinder at an angle of 40°, whereas light rays from the indicator notches are incident at angles of 10° or less. Differences in incident angle and/or differences in signal strength (as, for example, compared to threshold values) can be used to eliminate artifacts. Light from sources other than indicators (for example, the scattered light giving rise to leftmost area or artifact in FIG. 12) can also be prevented by placing an optical stop 1120 at the bottom of the syringe as illustrated in FIG. 13 or it can be blocked, for example, by using collimated detectors.

Figure 13:
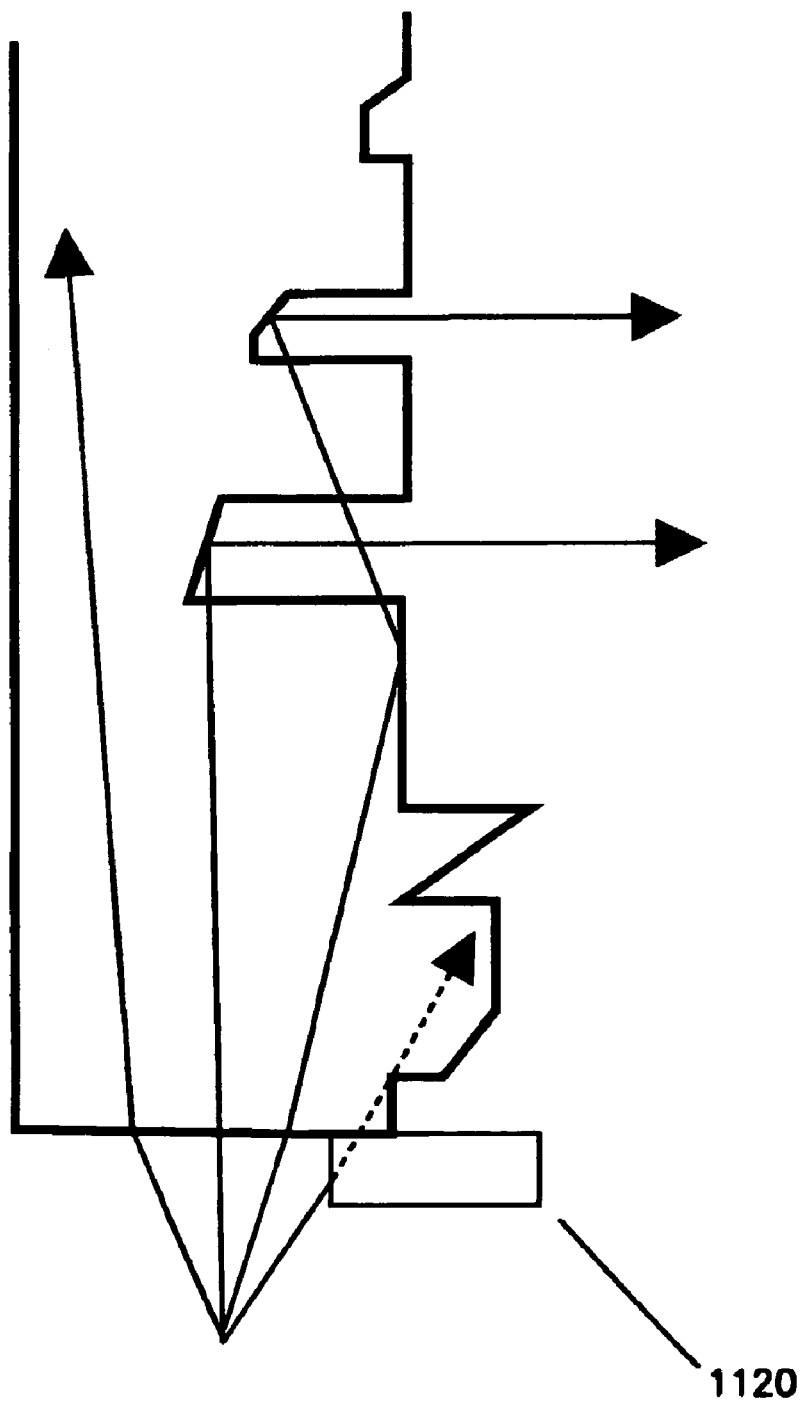
FIG. 13 illustrates examples of light rays reflecting off indicators that originate from a combination of direct incidence and incidence via internal reflection.

In FIG. 12, the image areas from the last two indicator notches are noticeably broadened as the rays that reflect off those indicator notches originate from a combination of direct incidence and incidence via internal reflection off the outer surface of the syringe as represented in FIG. 13.

Figure 14:
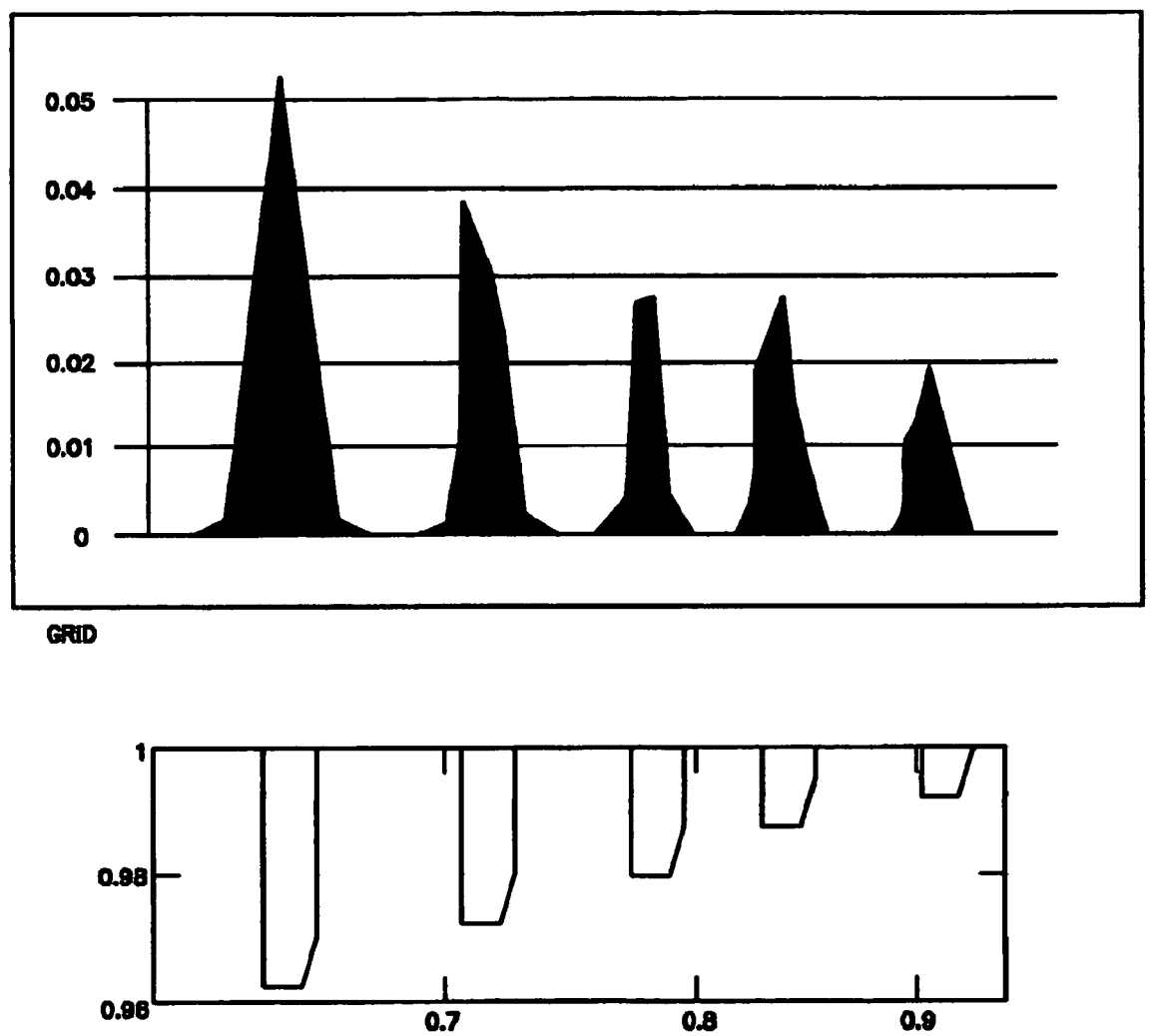
FIG. 14 illustrates the total brightness of each spot on an imaging cylinder shown above its corresponding indicator notch for the model design of FIG. 11.

FIG. 14 shows the total brightness of each spot on the imaging cylinder, shown above its corresponding indicator notch. There was a 3:1 ratio between the brightness of the first indicator notch image and that of the last. It is possible to adjust this by progressively increasing the reflector sizes from first to last.

Figure 15:
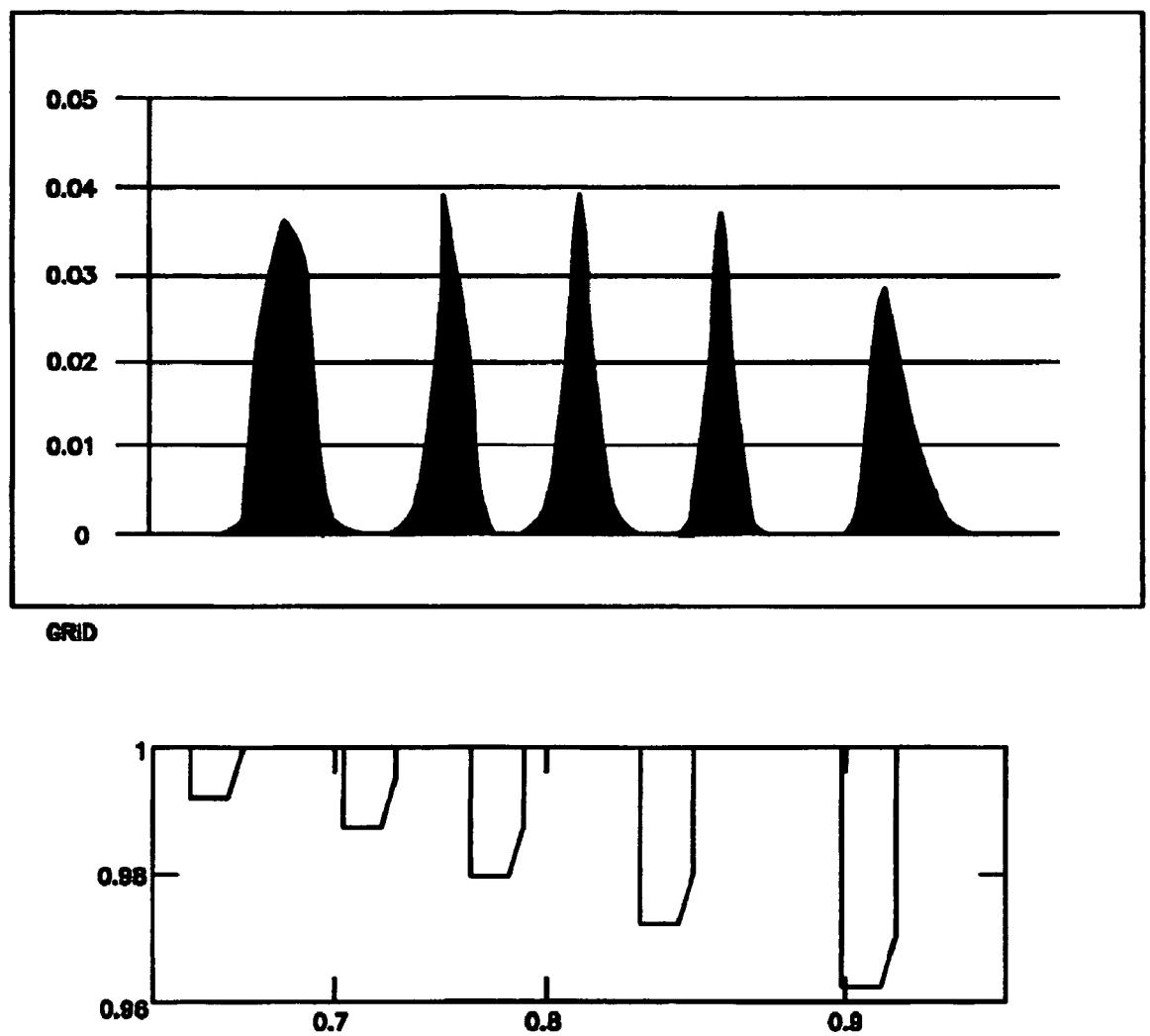
FIG. 15 illustrates the total brightness of each spot on an imaging cylinder shown above its corresponding indicator notch for a model design in which the order of indicator notches is reversed from that of FIG. 14.

Alternatively, by reversing the order of the indicator notches such that the shallowest indicator notch is placed closest to the energy source and the deepest indicator notch is placed farthest from the energy source, brightness/intensity reductions can be substantially eliminated. In that regard, FIG. 15 shows the total brightness of each spot on the imaging cylinder, shown above its corresponding indicator notch in such an embodiment. As illustrated, there is very little reduction in brightness between the first indicator notch and the last indicator notch in this embodiment.

Preferably, light transmitted to a sensor (as measured, for example, in brightness or signal strength) is sufficient such that the interaction of light with an indicator is readily detectable using commercially available, inexpensive sensors and light sources. An example of a suitable sensor for use in the present invention is the SFH229FA (part number) photodiode available from OSRAM, a corporation headquartered in Munich, Germany. An example of a suitable light source for use in the present invention is the HSDL-4230 (part number) LED available from Hewlett-Packard, a corporation headquartered in Palo Alto, Calif.

Figure 16A:
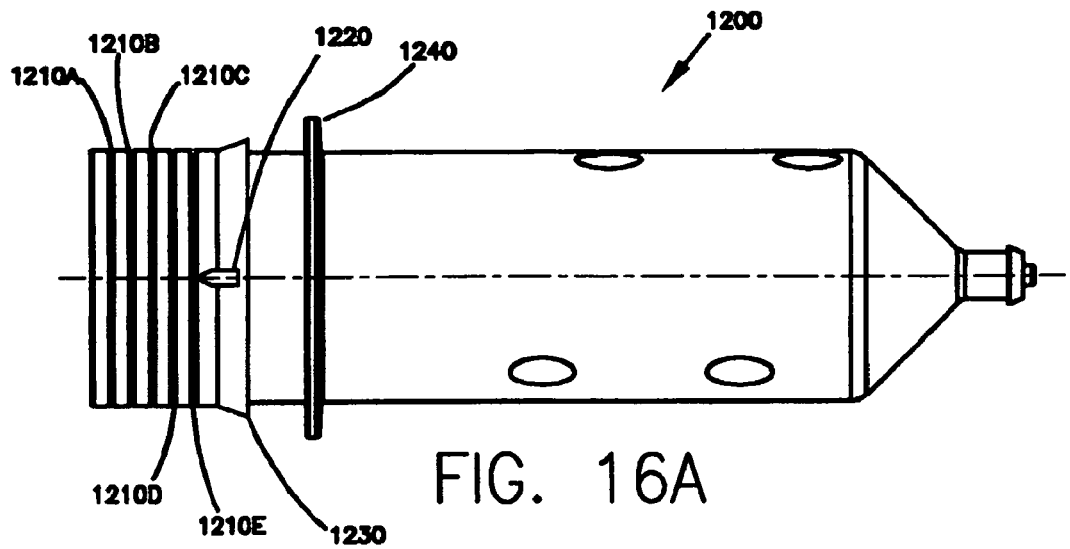
FIG. 16A illustrates a side view of an embodiment of a syringe of the present invention in which the depth of indicator notches increases with increasing distance from a light source.
Figure 16B:
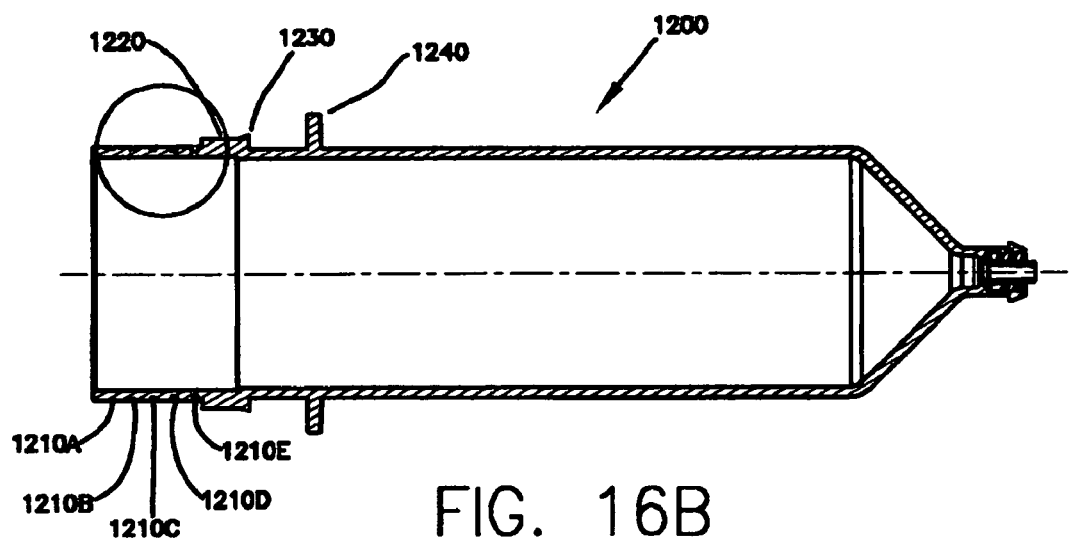
FIG. 16B illustrates a side, cross-sectional view of the syringe of FIG. 16A.
Figure 16C:
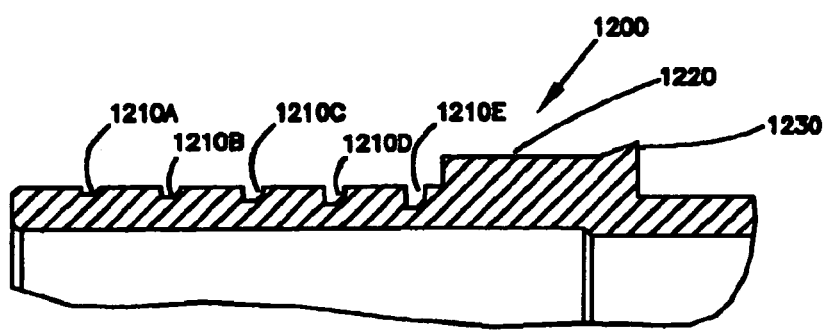
FIG. 16C illustrates an expanded view of the encircled area of FIG. 16B.

FIGS. 16A-16C illustrate an embodiment of a syringe 1200 in which indicator notches 1210*a*-1210*e* increase in depth with increasing distance from a light source (not shown in FIGS. 16A-16C) as described in connection with FIG. 15. FIG. 16C illustrates an expanded view of indicator notches 1210*a*-1210*e* (that is, the encircled portion of FIG. 16B) for one embodiment of syringe 1200. In that embodiment, the depth of indicator notches 1210*a*-1210*e* is 0.012 in., 0.020 in., 0.028 in., 0.036 in. and 0.044 in., respectively. Indicator notches 1210*a*-1210*e* are preferably placed at a rearward position on syringe 1200 to position indicator notches 1210*a*-1210*e* as close as possible to the light source as well as to reduce or prevent artifacts arising from other syringe components. For example, elements 1220, engagement flange 1230 and drip flange 1240 can each cause artifacts in an image plane as illustrated, for example, by the leftmost image area of FIG. 12. Placing indicator notches 1210*a*-1210*e* between the energy/light source and such syringe components greatly reduces the likelihood of undesirable artifacts.

Figure 16D:
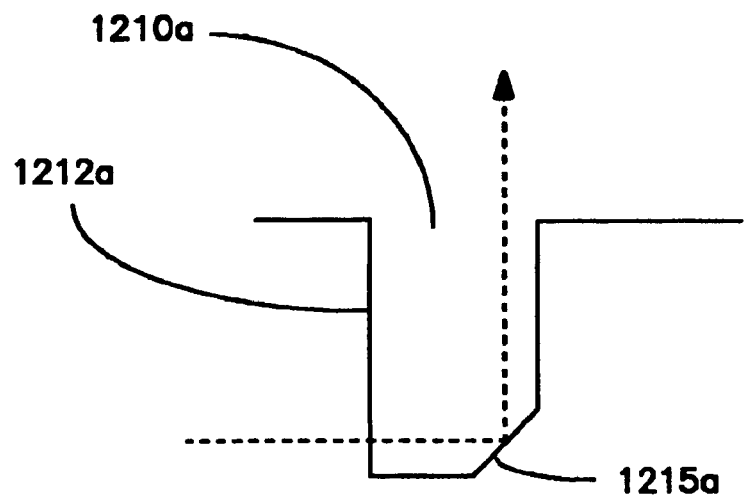
FIG. 16D illustrates an expanded view of one of the indicator notches of FIGS. 16A through 16C.

FIG. 16D illustrates an expanded view of indicator notch 1210*a* of FIGS. 16A through 16C. As illustrated in FIG. 16D, a light ray first passes through a generally perpendicular wall 1212*a* of indicator notch 1210*a* and then passes through the air to impinge upon surface 1215*a*, which reflects the light ray upward to a sensor (not shown in FIG. 16D).

Figure 16E:
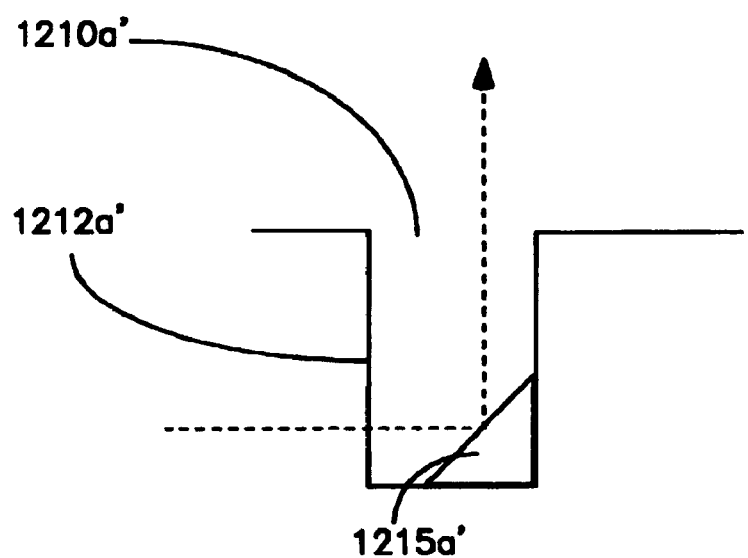
FIG. 16E illustrates an embodiment of an indicator notch including an attached reflective surface.

Surface 1215*a* in FIG. 16D is a portion of the syringe wall angled at an approximately 45° angle to light rays propagating lengthwise through the wall of syringe 1200. FIG. 16E illustrates another embodiment of an indicator notch 1210*a*'.

In the embodiment of FIG. 16E, a light ray first passes through a generally perpendicular wall 1212a' of indicator notch 1210a' and then passes through the air to impinge upon surface 1215a', which reflects the light ray upward to a sensor (not shown in FIG. 16E). In the embodiment of FIG. 16E, reflective surface 1215a' is formed of a different material (preferably, a highly reflective material) than the material of syringe 1200.

Figure 17A:
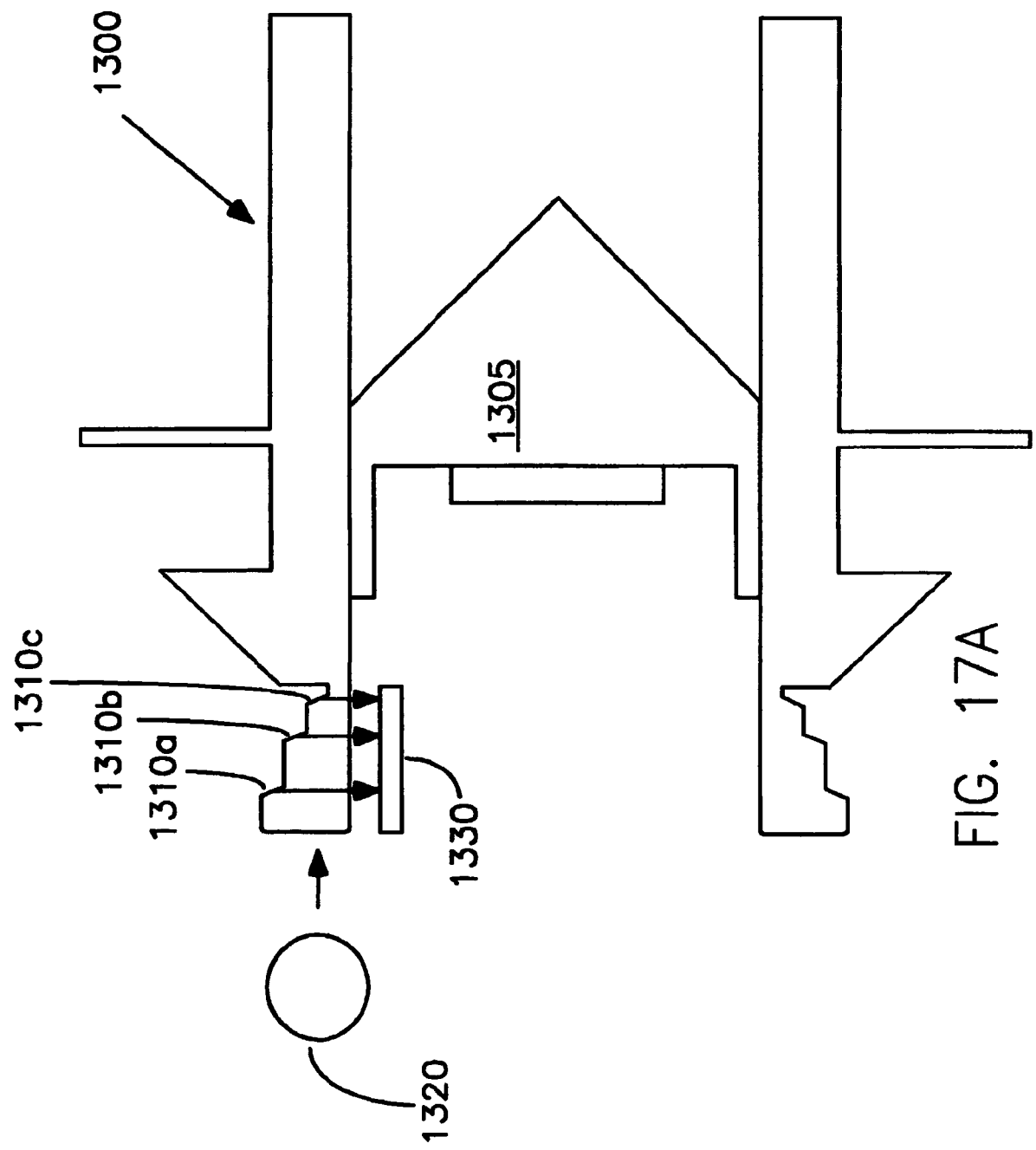
FIG. 17A illustrates a side, cross-sectional view of an embodiment of a syringe in which indicators redirect energy to one or more sensors positioned within the interior of the syringe.

FIG. 17A illustrates an embodiment of a rear portion of a syringe 1300 including indicators 1310a-1310c formed as angled steps in the exterior wall of syringe 1300. In one embodiment, indicators 1310a-1310c are angled at approximately 45° with respect to light rays propagated through the wall of syringe 1300 from light source 1320. In this embodiment, light rays from light source 1320 are reflected at an angle of approximately 90° with respect to the orientation through which the light is propagated through the wall of syringe 1300 toward a sensor or sensors 1330 positioned on the interior side of the syringe wall. Reflection of light at generally right angles can facilitate positioning of a corresponding sensor or sensors for detection of reflected light. In this embodiment, indicators 1310a-1310c affect the light energy generally independently of each other. Preferably, sensor or sensors 1330 are positioned within the interior of the barrel of syringe 1300 to minimize or prevent interference with the movement of a plunger 1305 within the syringe barrel.

Figure 17B:
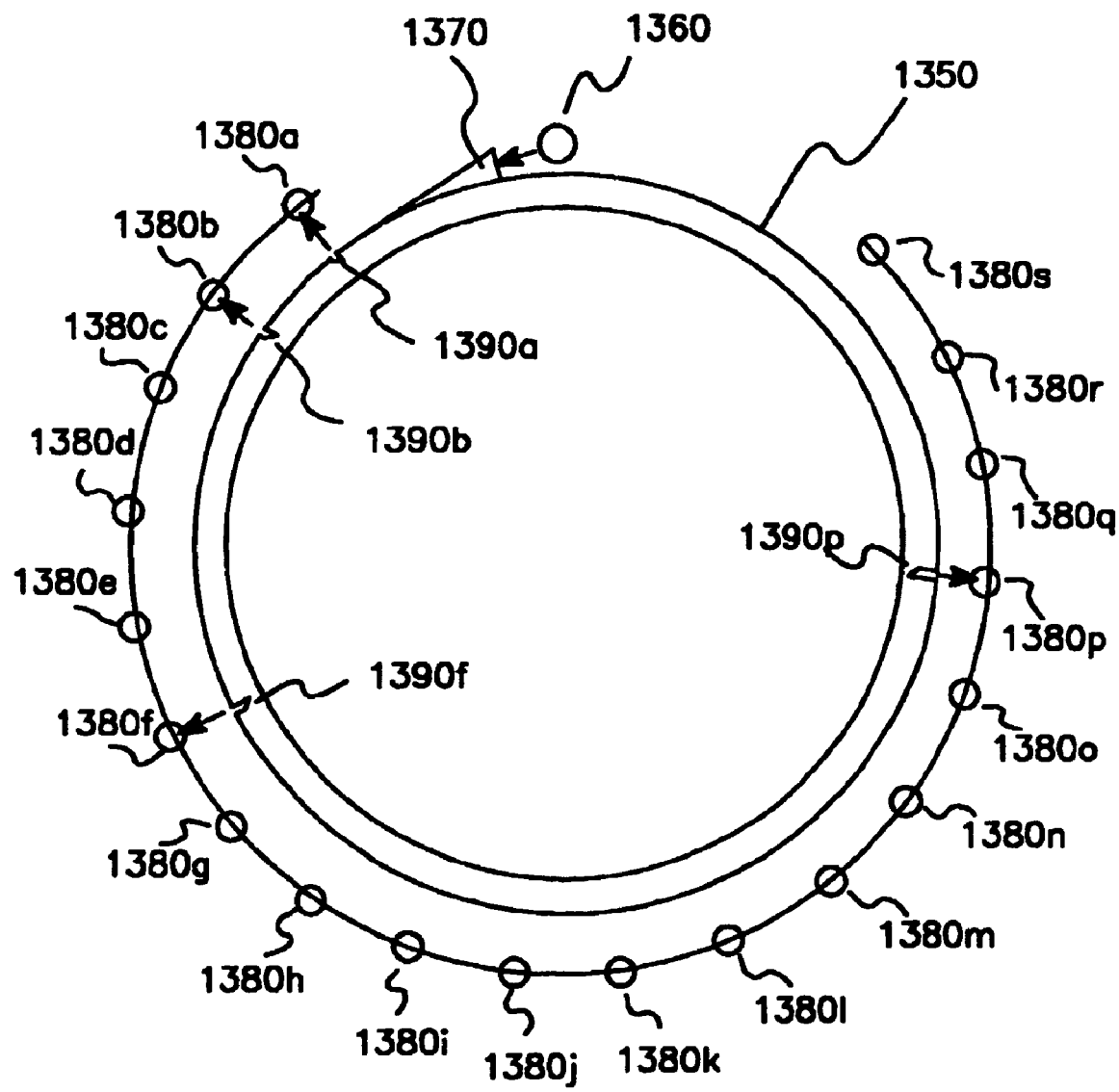
FIG. 17B illustrates a cross-sectional view of an embodiment of a syringe in which indicators are positioned around the circumference of the syringe.

In the embodiments described above, light is propagated generally linearly along, for example, the axial direction of a syringe, such as syringe 1300. However, light can also be propagated within or through the length of a radius or other curve in the present invention as illustrated in FIG. 17B. FIG. 17B illustrates a cross-section of a generally cylindrical encoded article such as a syringe 1350. A light source 1360 is used to transmit light through a port 1370 and into the barrel of syringe 1350. The light then propagates around the radius of syringe 1350 within the wall thereof. A series of sensors 1380a-1380s are preferably positioned outside the circumference of syringe 1350 at various positions to receive light redirected by indicators positioned about the circumference of syringe 1350 such as indicators 1390a, 1390b, 1390f and 1390p illustrated in FIG. 17B. Preferably, the material of syringe 1350 is chosen such that light traveling around syringe 1350 does not strike the interface between syringe 1350 and the surrounding air at an angle less than the critical angle, thereby providing for internal reflectance of the light as described above.

Providing indicator/sensor pairs about the radius or circumference of an encoded article such as syringe 1350 rather than or in addition to providing such indicator/sensor pairs along the axial length of such an article can provide additional space for additional indicator/sensor pairs to provide for additional encoded configurations. Moreover, a plurality of sets of indicator/sensor pairs oriented about the circumference of an encoded article can be placed at different axial positions along the axial length of the encoded article to provide even more encoded configurations.

In addition to transmitting or propagating energy (for example, light energy) through a length of material or an encoder (for example, a syringe wall) as set forth in the above examples, energy can also be transmitted through a medium adjacent to an encoder to interact with indicators of the present invention. In such embodiments of the present invention, the indicators can, for example, be surface features of the encoder that are positioned within or extend into the path of the energy being transmitted through a medium adjacent to the encoder.

Figure 18A:
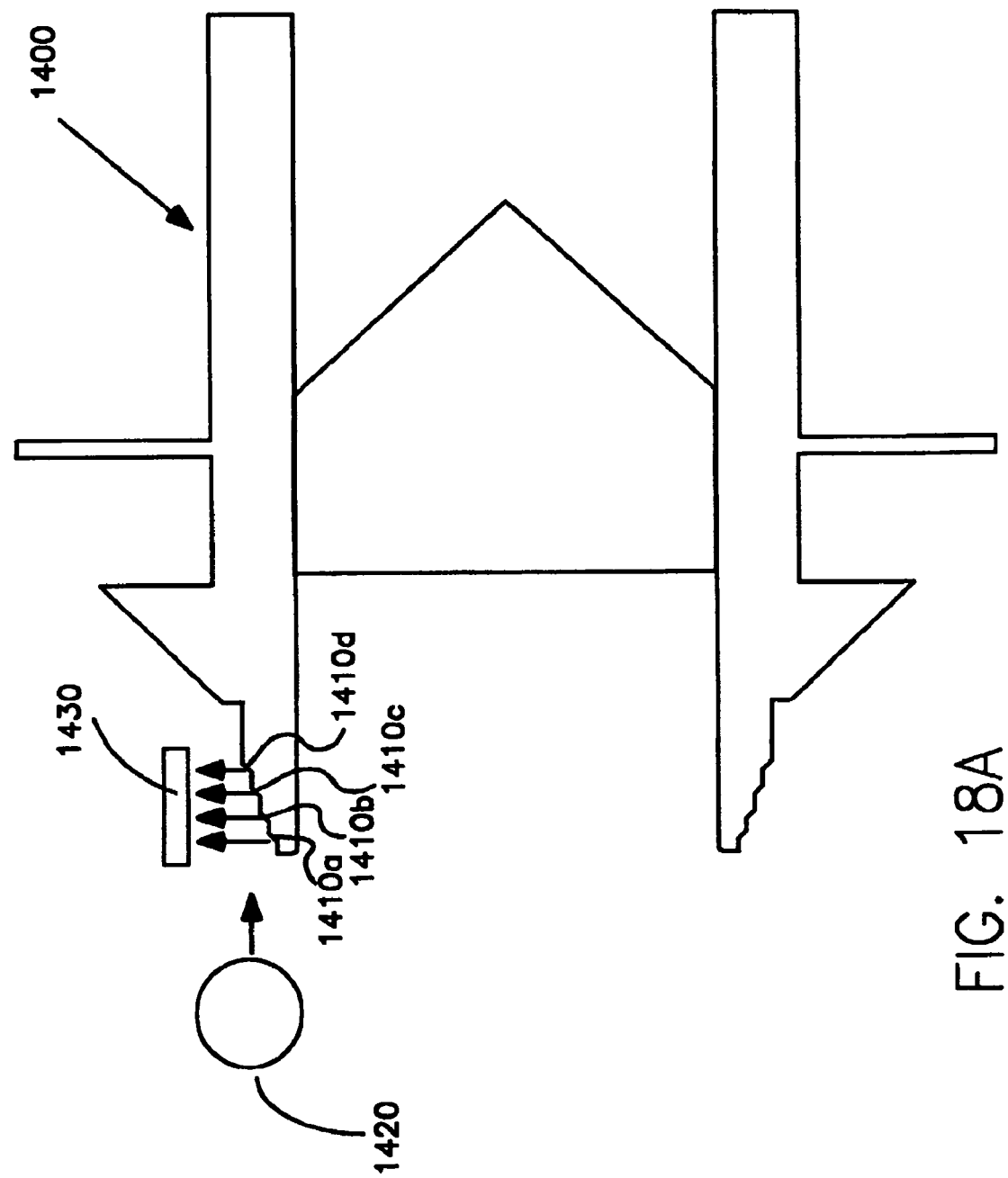
FIG. 18A illustrates a side, cross-sectional view of an embodiment of a syringe in which indicators redirect energy propagated along an exterior surface of the syringe to one or more sensors.

For example, FIG. 18A illustrates an embodiment of a rear portion of a syringe 1400 including indicators 1410a-1410d formed as angled steps in the exterior wall of syringe 1400. In one embodiment, indicators 1410a-1410d are angled at approximately 45° with respect to light rays propagated from light source 1420 in a direction generally parallel to the axis of syringe 1400 through, for example, the air surrounding the exterior wall of syringe 1400. In this embodiment, light rays from light source 1420 are reflected at an angle of approximately 90° with respect to the orientation through which the light is propagated through the air surrounding syringe 1400 toward a sensor or sensors 1430 positioned adjacent the exterior side of the syringe wall. Indicators 1410a-1410d can also interact with the energy from an energy source in other manners (for example, absorbance, fluorescence, etc.) as described above. In this embodiment, indicators 1410a-1410d affect the light energy generally independently of each other.

Figure 18B:
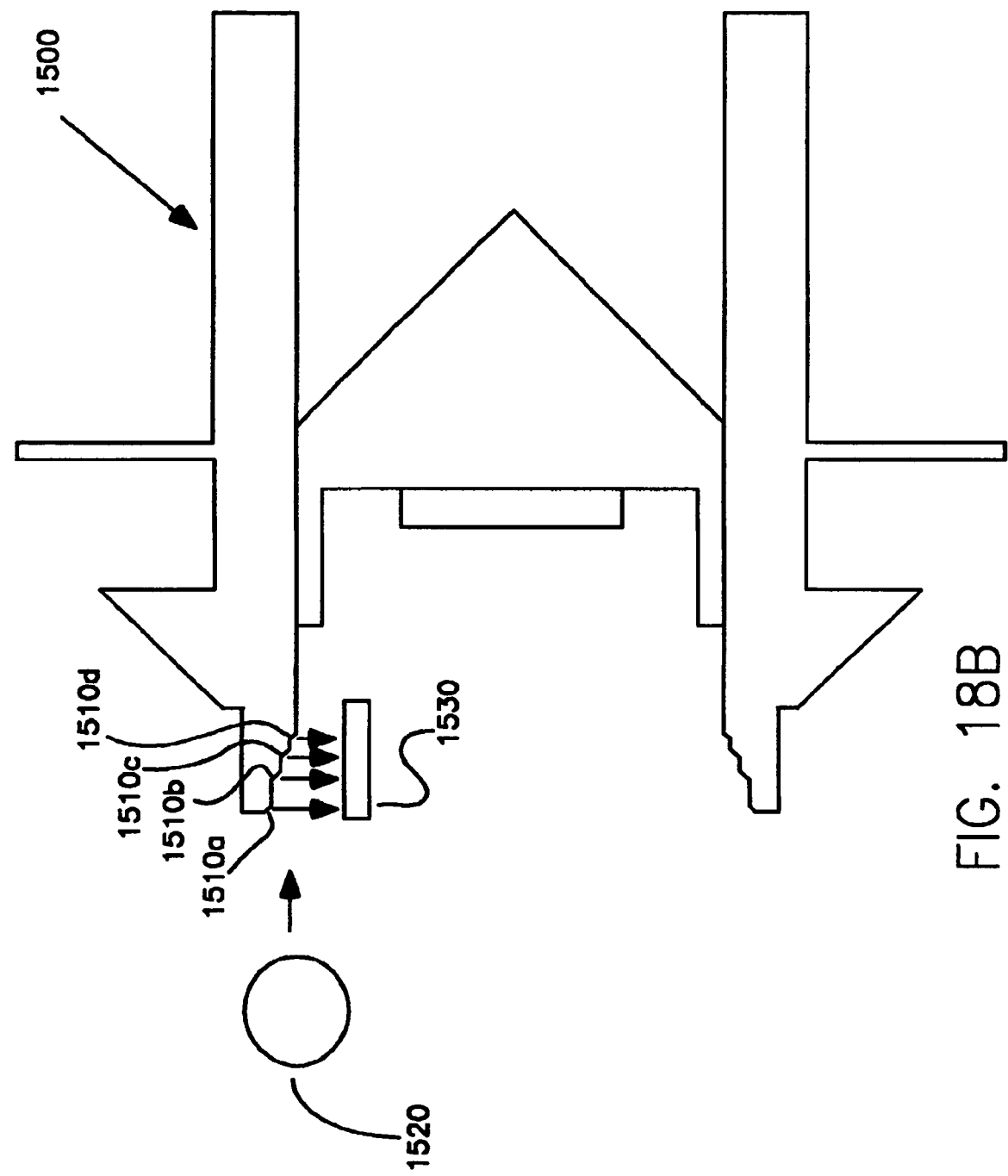
FIG. 18B illustrates a side, cross-sectional view of an embodiment of a syringe in which indicators redirect energy propagated along an interior surface of the syringe to one or more sensors.
Figure 18C:
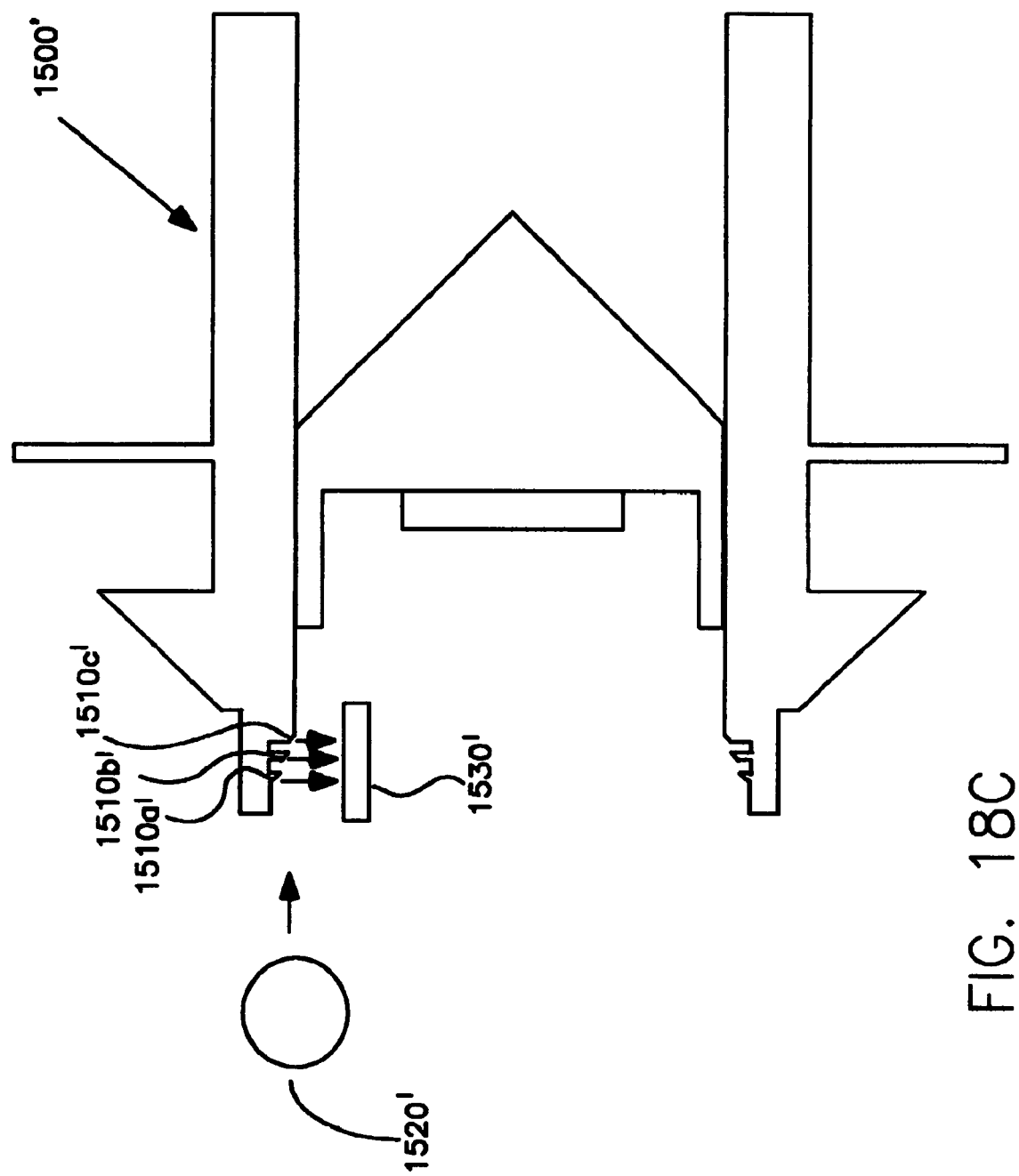
FIG. 18C illustrates a side, cross-sectional view of another embodiment of a syringe in which indicators redirect energy propagated along an interior surface of the syringe to one or more sensors.

In FIG. 18B, syringe 1500 includes indicators 1510a-1510d formed as angled steps in the interior wall of syringe 1500. In this embodiment, indicators 1510a-1510d are angled at approximately 45° with respect to light rays propagated from light source 1520 generally parallel to the axis of syringe 1500 through, for example, the air surrounding the interior wall of syringe 1500. The light rays from light source 1520 are reflected at an angle of approximately 90° with respect to the orientation through which the light is propagated through the air surrounding syringe 1500 toward a sensor or sensors 1530 positioned adjacent the interior side of the syringe wall. FIG. 18C illustrates another embodiment of a syringe 1500' including extending indicators 1510a'-1510c' that extend into the path of light energy from a light source 1520'. Each of extending indicators 1510a'-1510c' includes a surface angled at approximately 450 with respect to light rays propagated from light source 1520' to reflect the light rays to a sensor 1530'.

FIGS. 19A through 19H illustrate an embodiment of a sensing assembly 1600 that can be used in the injector systems of the present invention. Sensor assembly 1600 is positioned within seating 2010 of a powered injector 2000 in the vicinity of a syringe interface 2020 of powered injector 2000. Sensor assembly 1600 includes a light emitter or light source 1610 such as a light emitting diode. Suitable light emitting diodes for light source 1610 include an 800 nM diode emitter available from Osram Opto Semiconductors of San Jose, Calif., under product number SFH 484-2 and the HSDL-4230 LED available from Hewlett-Packard. Light source 1610 is in electrical connection with a printed circuit board 1620, which controls operation of light source 1610. Sensing assembly 1600 also includes a plurality of sensors 1630a-1630e. Light from light source 1610 travels or propagates in an axial direction through the wall of syringe 1800. Indicators such as indicators 1810a, 1810c and 1810e reflect light to sensors 1630a, 1630c and 1630e as described above. In one embodiment, sensors 1630a-1630e are 3 mm silicon photodiodes available from Osram Opto Semiconductors under product number SFH 229. Sensors 1630a-1630e are in electrical connection with a printed circuit board 1640.

Sensor assembly 1600 preferably assists in achieving suitable alignment of the wall of syringe 1800 with light source 1610. Sensor assembly also preferably biases or positions syringe 1800 against or in close proximity with a translucent surface 1650. Biasing or positioning syringe 1800 in close proximity with surface 1650 substantially reduces or eliminates the formation of fluid droplets (for example, leaked contrast) on the surface of syringe 1800. A fluid droplet can act as a lens to redirect stray light from emitter 1610, which can result in an incorrect reading. Preferably, the distance between syringe 1800 and surface 1650 is less than 0.020 in. to prevent formation of fluid droplets therebetween. Sensor assembly 1600 can, for example, include one or more biasing or abutment members 1660. Surface 1650 and abutment member 1660 create a slot or gap 1662 therebetween in which a portion of syringe 1800 is seated. Abutment member(s) 1660 positions the exterior surface of syringe 1800 in close proximity with surface 1650 as described above. As illustrated, for example, in FIGS. 19B and 19C, translucent surface 1650 and abutment member 1660 can be molded as an integral subassembly 1670, which assists in reducing stacked tolerance problems that can result in multi-component assemblies. In one embodiment, subassembly 1670 was molded from Makrolon 2405 polycarbonate available from Bayer Corporation of Pittsburgh, Pa. The translucent polycarbonate included a dye (available from Bayer Corporation under product number 7881) that substantially prevents ambient light from passing through surface 1650 and the remainder of subassembly 1670, but allows passage of light in the operative infrared range of light source 1610 and sensors 1630a-1630e.

Sensor assembly 1600 further includes a sensor support member 1680 that attaches to subassembly 1670. Sensor support member 1680 is properly aligned with subassembly 1670 via cooperation of dowel pins 1682 on sensor support member 1680 with holes 1672 formed in subassembly 1670. Sensor support member 1680 further includes holes or passages 1684a-1684e, which align with sensors 1630a-1630e when sensor printed circuit board 1640 is seated in seating 1676 of sensor support member 1680. Passages 1684a-1684e allow light redirected by, for example, indicators 1810a, 1810c and 1810e to pass through translucent surface 1650 and impinge upon sensors 1630a, 1630c and 1630e. Sensor printed circuit board 1640 and sensor support member 1680 can, for example, be connected to subassembly 1670 by fasteners 1690 (for example, screws).

Emitter printed circuit board 1620 is properly aligned with and attached to sensor support member 1680 by cooperation of fasteners 1692 (for example, screws), which pass through holes 1622 in emitter printed circuit board 1620 and into guides 1689 in sensor support member 1680. Connection of emitter printed circuit board 1620 to sensor support member 1680 positions light source 1610 so that light therefrom passes through translucent subassembly 1650 to travel axially through slot or gap 1662 formed between surface 1650 and abutment members 1660 as described above.

In the embodiment of FIGS. 19A through 19H, sensor printed circuit board 1640 includes test emitters 1642a-1642e (for example, infrared photo diodes available from Agilent Technologies of Palo Alto, Calif., under product number HSDL-4400-011). Test emitters 1642a-1642e can be used to test the operation of sensors 1630a-1630e. As illustrated by the arrow in FIG. 19D, for example, light emitted from test emitters 1642a-1642e can be reflected off an approximately 45° angled surface 1683 formed in sensor support member 1680 to impinge upon sensors 1630a-1630e, respectively.

For a syringe manufactured from PET as described above, preferred ranges of properties for emitter 1610 are described in Table 1 below.

TABLE 1

| Property | Preferred Value Range |
| --- | --- |
| Peak Wavelength | 850-950 nm |
| Spectral Width at FWHM | <50 nm |
| Radiance on axis Intensity | >75 mW/sr |
| Emission Angle | <20° |

TABLE 1-continued

| Property | Preferred Value Range |
| --- | --- |
| Maximum forward current at 25 kHz and 50% duty cycle | >100 mA |
| Optical rise and fall time | <4 µs |
| Bandwidth | >150 kHz |

For a syringe manufactured from PET as described above, preferred ranges of properties for sensors 1630a-e are described in Table 2 below.

TABLE 2

| Property | Preferred Value Range |
| --- | --- |
| Peak Sensitivity | 850-950 nm |
| Spectral Width (50% of max) | <±300 nm |
| Photocurrent Bias = 5 V, Irradiance = 1 mW/cm$^2$, λ = 900 nm | >10 µA |
| Dark Current | <10 nA |
| Acceptance half-angle | <20° |
| Rise and fall time | <4 µs |

For a syringe manufactured from PET as described above, preferred ranges of properties for test emitters 1642a-e are described in Table 3 below.

TABLE 3

| Property | Preferred Value Range |
| --- | --- |
| Wavelength | 850-950 nm |
| On axis intensity | >1 mW/sr |
| Half angle | >60° |

Figure 19A:
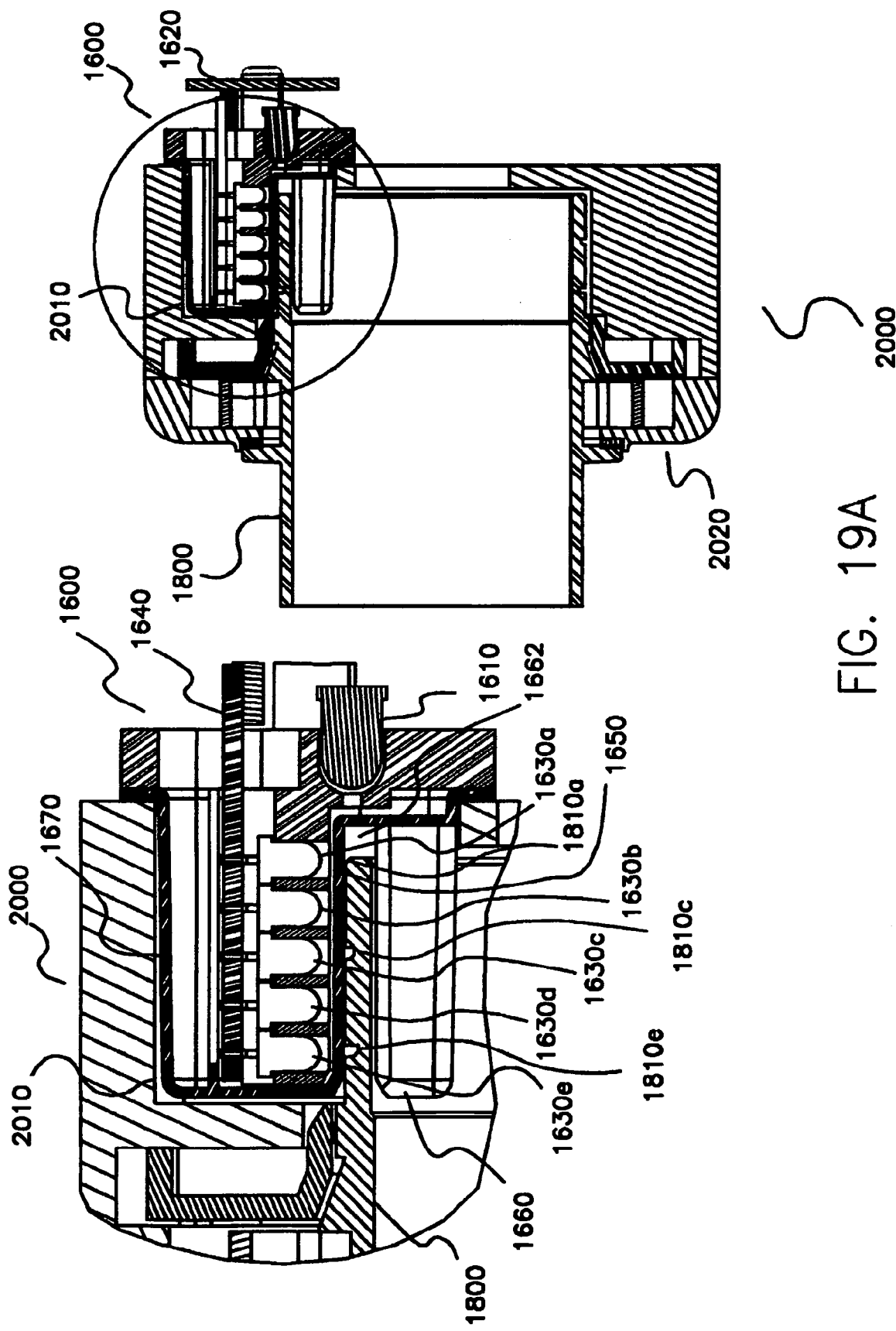
FIG. 19A illustrates a side, cross-sectional view of a sensor assembly of the present invention in operative connection with a syringe in which light is propagated axially through the syringe wall.
Figure 19B:
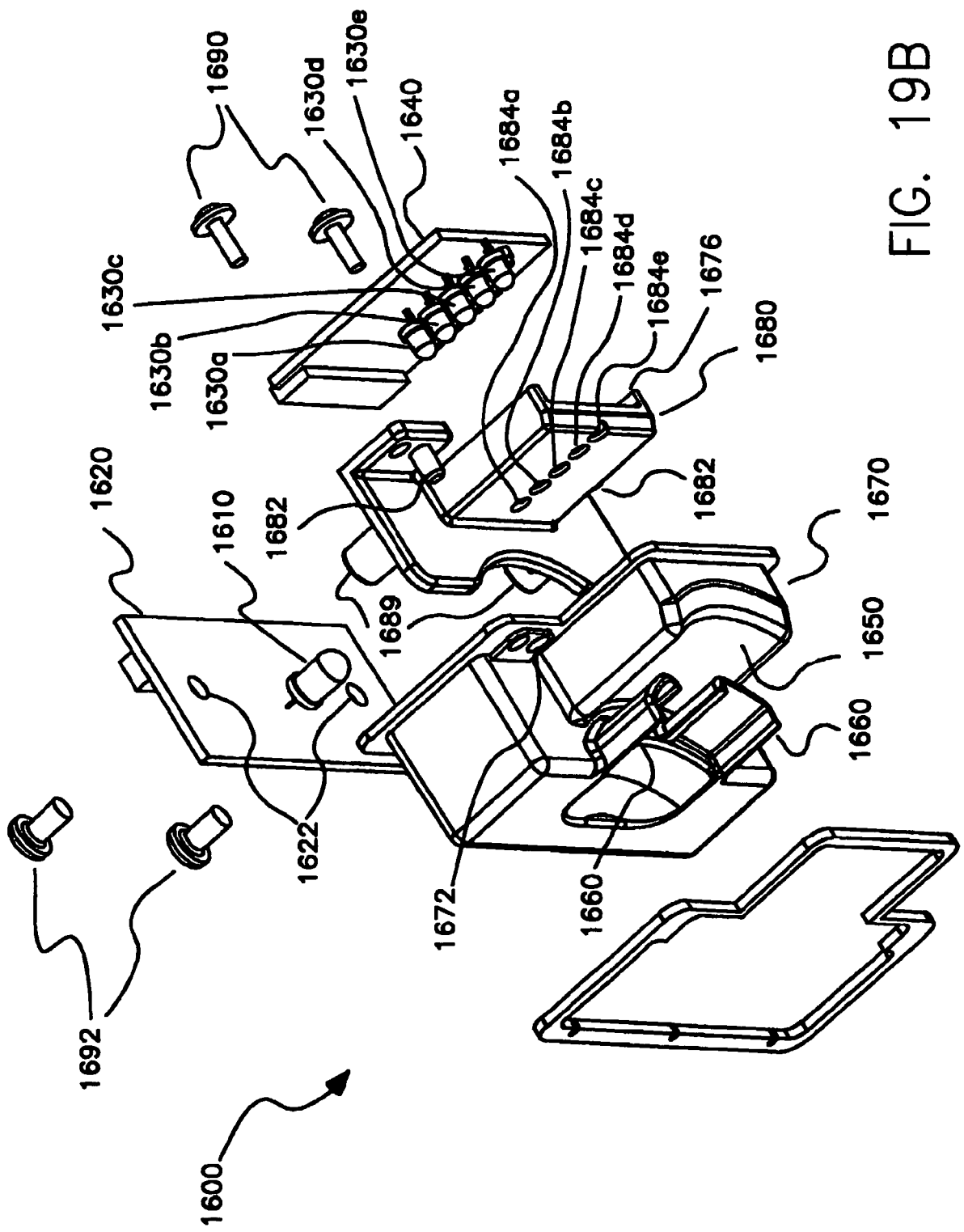
FIG. 19B illustrates a perspective view of the sensor assembly of FIG. 19A in a disassembled or exploded state.
Figure 19C:
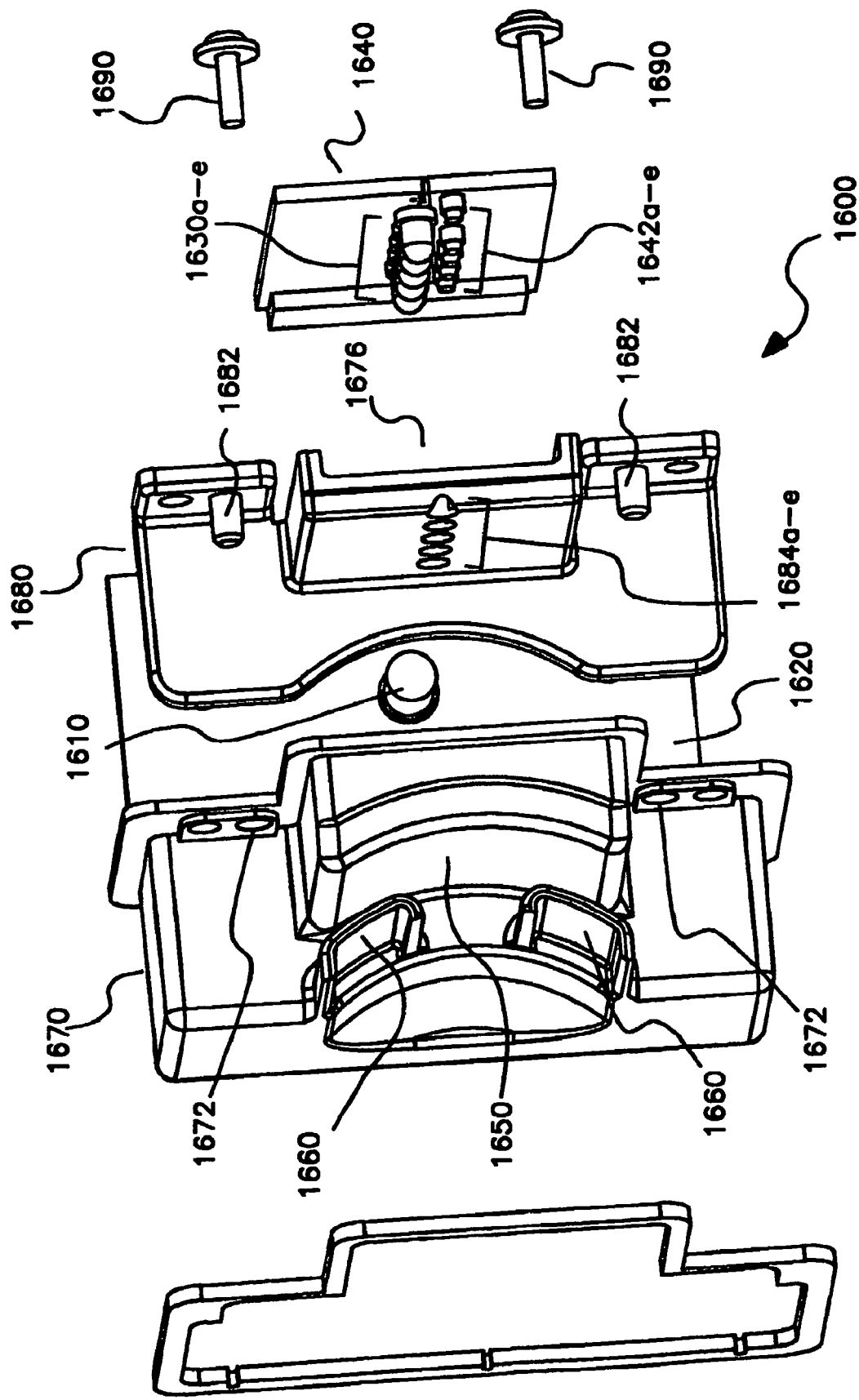
FIG. 19C illustrates another perspective view of the sensor assembly of FIG. 19A in a disassembled or exploded state.
Figure 19D:
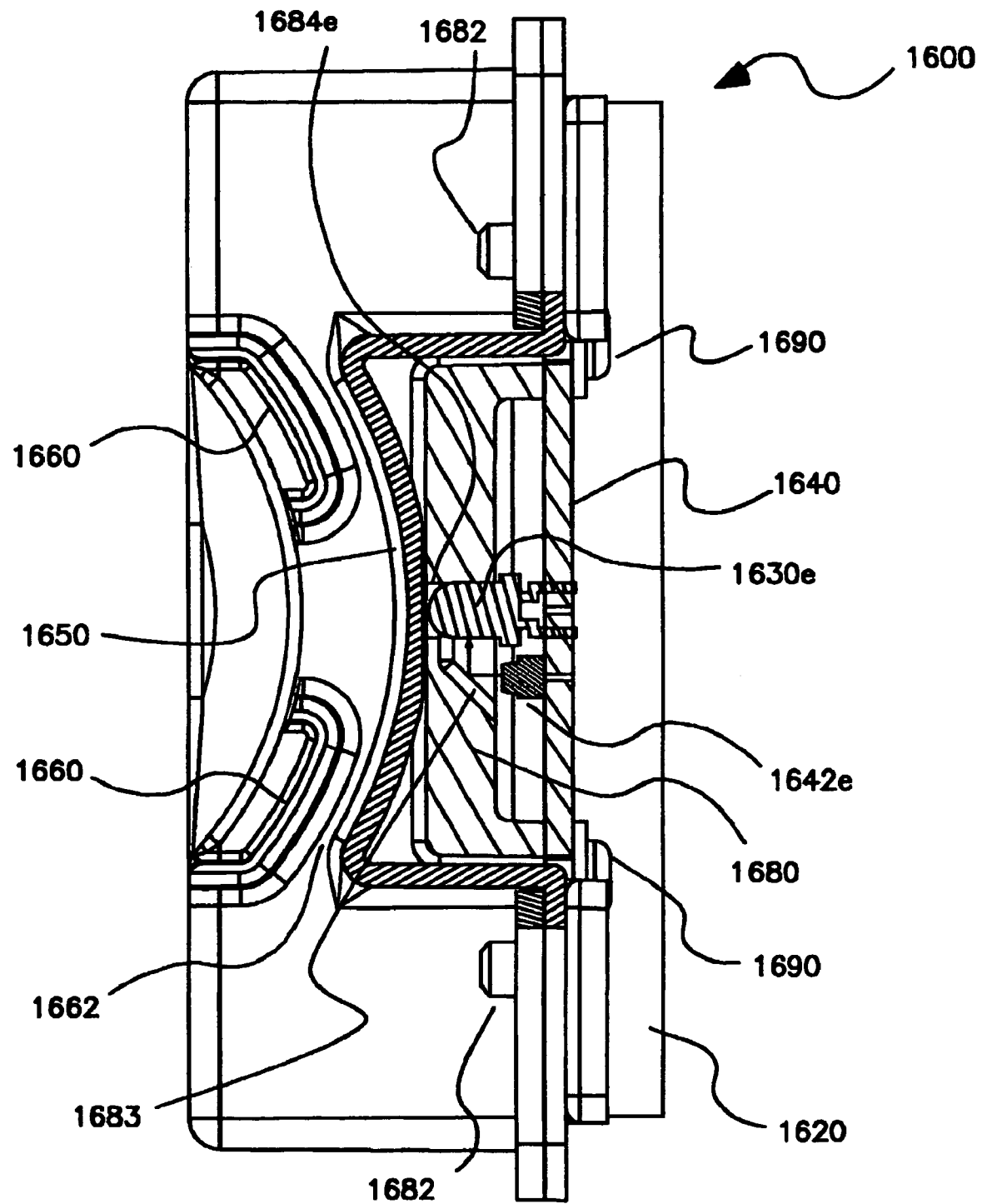
FIG. 19D illustrates a front cross-sectional view of the sensor assembly of FIG. 19A in an assembled state.
Figures 19E, 19F:
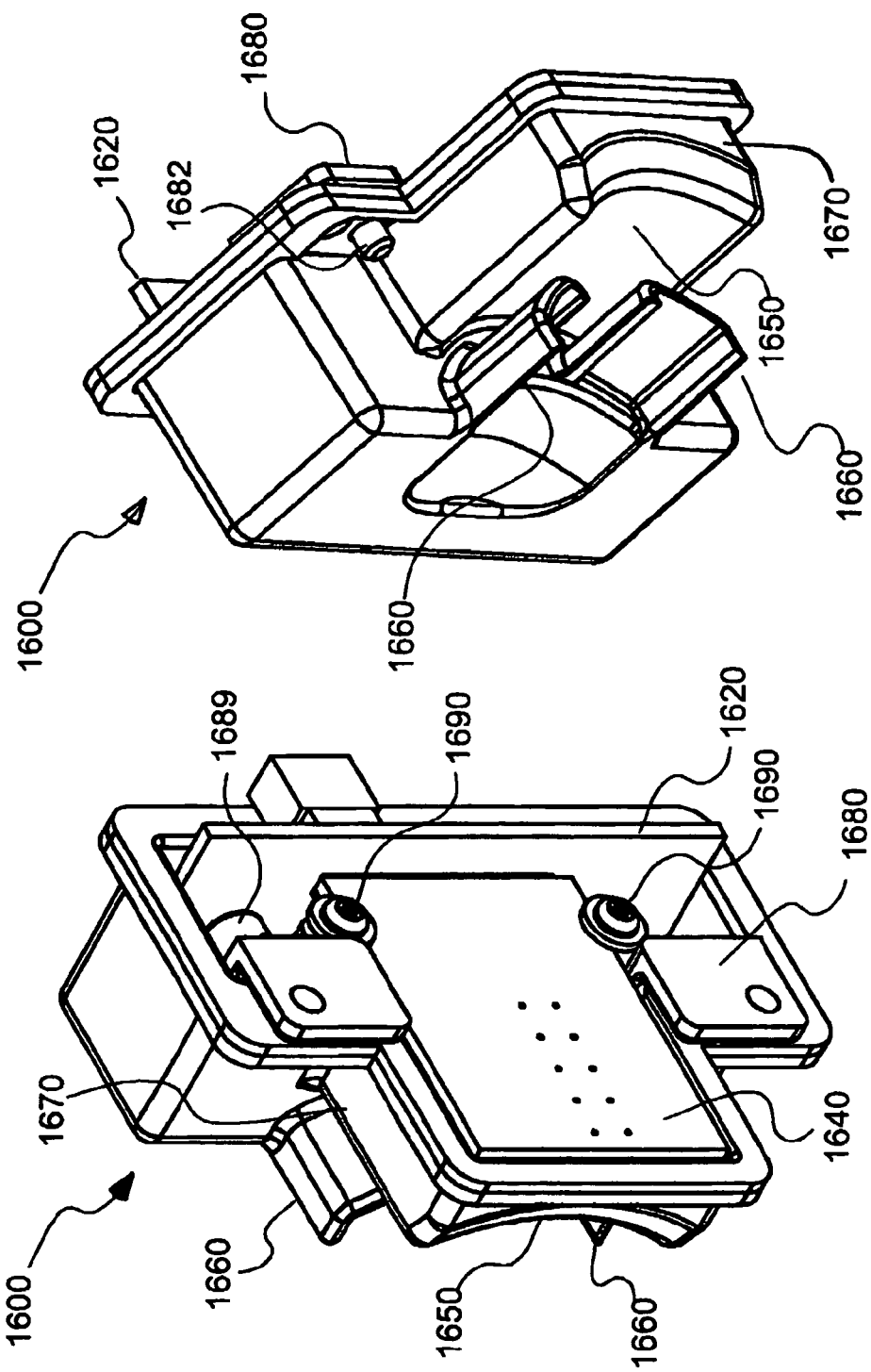
FIG. 19E illustrates a perspective view of the sensor assembly of FIG. 19A in an assembled state.
FIG. 19F illustrates another perspective view of the sensor assembly of FIG. 19A in an assembled state.
Figure 19G:
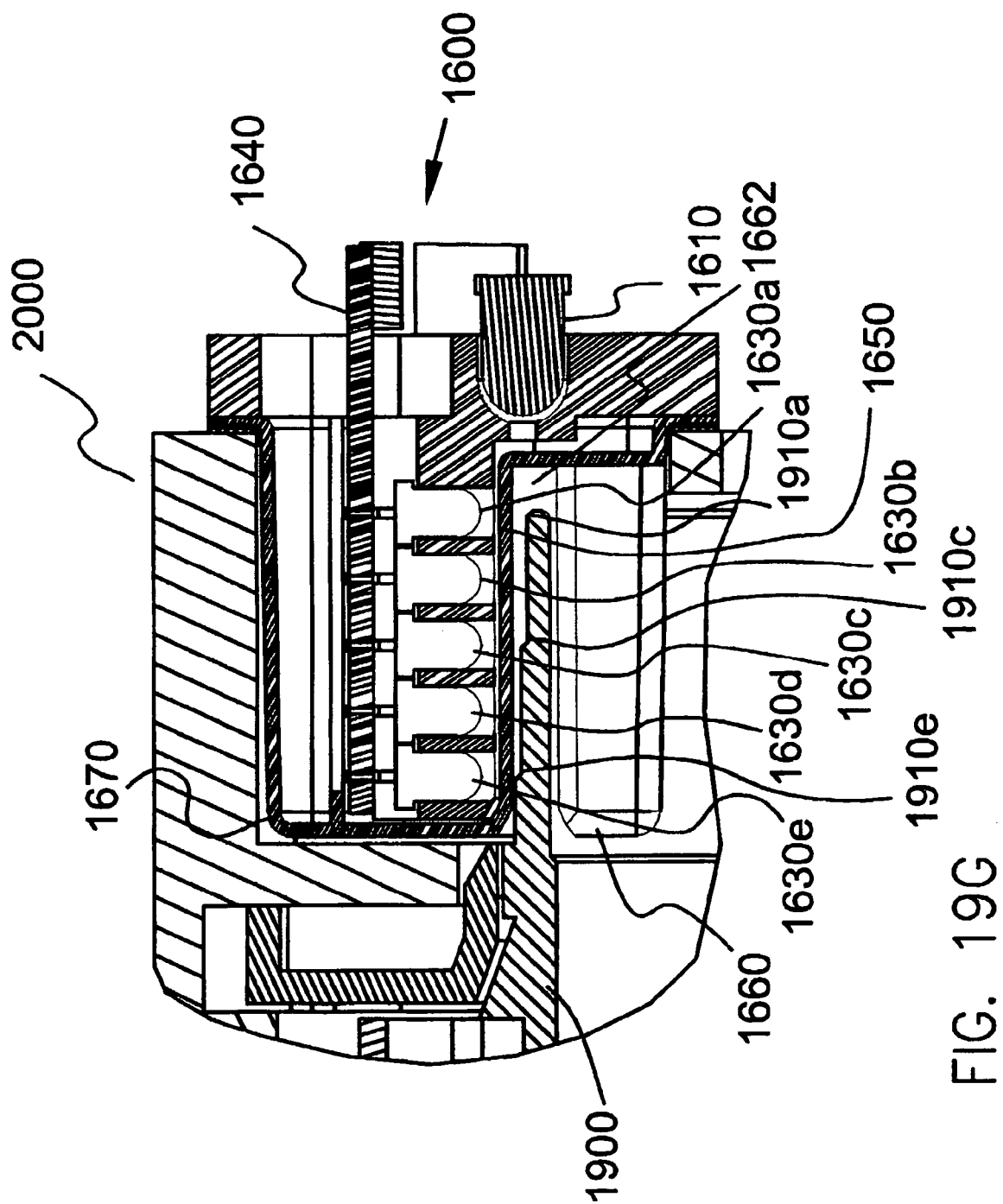
FIG. 19G illustrates a side, cross-sectional view of a sensor assembly of the present invention in operative connection with a syringe or an adapter in which light is propagated axially adjacent the syringe wall.

As illustrated in FIG. 19G, sensor assembly 1600 can also be used with a syringe or adapter 1900 in which light is transmitted through a medium (for example, air) adjacent to syringe or adapter 1900 to interact with indicators 1910a, 1910c and 1910e as described above.

Figure 19H:
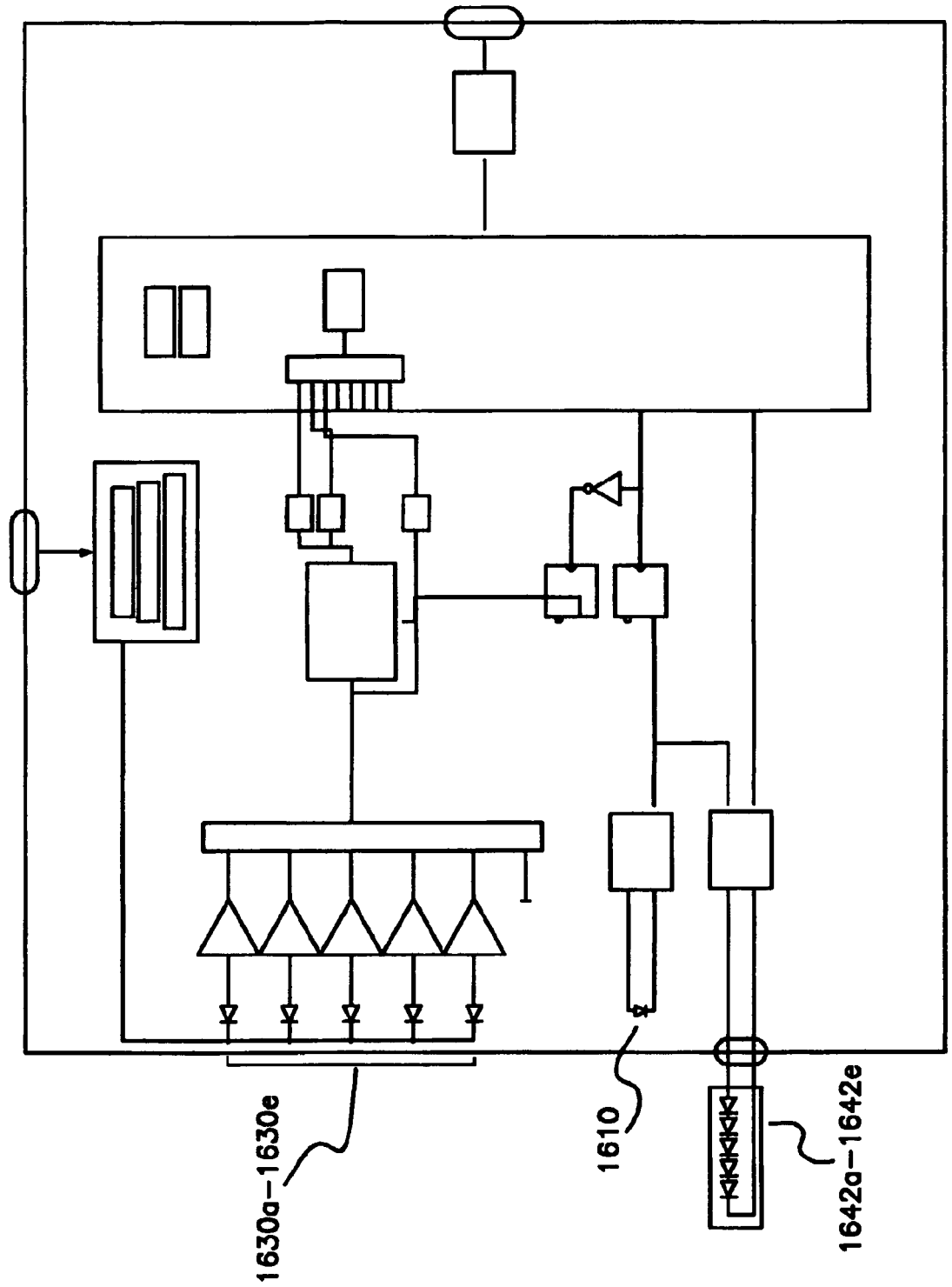
FIG. 19H illustrates a block diagram of one embodiment of the emitter and sensor printed circuit boards of the sensor assembly of FIG. 19A.

FIG. 19H illustrates a schematic block diagram of one embodiment of emitter printed circuit board 1620 and sensor printed circuit board 1640;

Although the present invention has been described in detail in connection with the above examples and embodiments, it should be appreciated that the present invention may be configured and conducted as appropriate for any application or context at hand. The embodiments described above are to be considered in all respects only as illustrative and not restrictive. The scope of the invention is defined by the following claims rather than the foregoing description. All changes to the claimed invention that fall within the meaning and range of equivalency of the claims are to be embraced within their scope.

What is claimed is:

1. An injector for use with an encoded syringe or an encoded syringe adapter, the injector comprising:
    an interface adapted to attach the syringe or the syringe adapter to the injector;
    a positioning subassembly comprising a translucent surface through which light can pass; and
    at least one abutment member spaced from the translucent surface to position the encoded syringe or the encoded syringe adapter seated in a gap formed between the translucent surface and the abutment member at a desired position relative to the translucent surface, at least one energy source disposed axially rearward of the positioning subassembly and adapted to direct energy in an axial direction; and at least one sensor adapted to detect energy impinging thereupon as a result of the encoding of the syringe or the syringe adapter;

wherein the at least one energy source comprises a light source.

2. The injector of claim 1 wherein the translucent surface is positioned sufficiently closely to the syringe or syringe adapter to prevent formation of fluid droplets between the syringe or syringe adapter and the translucent surface.

3. The injector of claim 2 wherein the at least one sensor is positioned on the side of the translucent surface opposite the side upon which the abutment member is positioned.

4. The injector of claim 3 wherein the at least one sensor comprises a plurality of sensors.

5. The injector of claim 4 wherein the plurality of sensors are connected to the positioning subassembly.

6. The injector of claim 5 wherein the light source is connected to the positioning subassembly.

7. The injector of claim 4 wherein the at least one light source is positioned to transmit light in an axial direction in the gap formed between the translucent surface and the abutment member.

8. The injector of claim 7 wherein the gap is aligned with the light source so that the light source is operable to propagate light through a translucent region of a wall of the syringe or syringe adapter in an axial direction.

9. The injector of claim 8 wherein each of the plurality of sensors is adapted to sense light impinging thereon which is redirected from a unique axial position on the syringe or the syringe adapter.

10. The injector of claim 9 wherein each of the plurality of sensors is positioned at a different axial position on the injector.

11. The injector of claim 7 wherein the sensor assembly further comprises a testing light source for each sensor to test the operability of each sensor.

12. The injector of claim 1 wherein the light source is operable to propagate light along a surface of a wall of the syringe or the syringe adapter in an axial direction.

13. The injector of claim 12 wherein the injector comprises a plurality of sensors.

14. The injector of claim 13 wherein each of the plurality of sensors is adapted to sense light impinging thereon which is redirected from a unique axial position on the syringe or the syringe adapter.

15. The injector of claim 12 wherein the light source is operable to propagate light along an inner surface of a wall of the syringe or the syringe adapter in an axial direction.

16. The injector of claim 12 wherein the light source is operable to propagate light along an outer surface of a wall of the syringe or the syringe adapter in an axial direction.

17. The injector of claim 1 wherein the at least one sensor comprises a plurality of sensors and the injector further comprises a testing mechanism to test the operation of each of the plurality of sensors.

18. The injector of claim 17 wherein the testing mechanism comprises a plurality of testing light sources, each of the testing light sources being adapted to transmit light to one of the plurality of sensors.

19. An injector for use with an encoded syringe or an encoded syringe adapter, the injector comprising:

an interface adapted to attach the syringe or the syringe adapter to the injector;

at least one energy source adapted to propagate energy in an axial direction;

at least one sensor adapted to detect energy impinging thereupon as a result of the encoding of the syringe or the syringe adapter; and a sensor assembly comprising:

a positioning subassembly comprising a translucent surface through which light can pass; and at least one abutment member spaced from the translucent surface to position the encoded syringe or the encoded syringe adapter seated in a gap formed between the translucent surface and the abutment member at a desired position relative to the translucent surface, wherein the at least one energy source comprises a light source, wherein the light source is operable to propagate light along a surface of a wall of the syringe or the syringe adapter in an axial direction.

20. The injector of claim 19 wherein the translucent surface is positioned sufficiently closely to the syringe or syringe adapter to prevent formation of fluid droplets between the syringe or syringe adapter and the translucent surface.

21. The injector of claim 20 wherein the at least one sensor is positioned on the side of the translucent surface opposite the side upon which the abutment member is positioned.

22. The injector of claim 21 wherein the at least one sensor comprises a plurality of sensors.

23. The injector of claim 22 wherein the plurality of sensors are connected to the positioning subassembly.

24. The injector of claim 23 wherein the light source is connected to the positioning subassembly.

25. The injector of claim 22 wherein the at least one light source is positioned to transmit light in an axial direction in the gap formed between the translucent surface and the abutment member.

26. The injector of claim 25 wherein the gap is aligned with the light source so that the light source is operable to propagate light through a translucent region of a wall of the syringe or syringe adapter in an axial direction.

27. The injector of claim 26 wherein each of the plurality of sensors is adapted to sense light impinging thereon which is redirected from a unique axial position on the syringe or the syringe adapter.

28. The injector of claim 27 wherein each of the plurality of sensors is positioned at a different axial position on the injector.

29. The injector of claim 19 wherein the at least one sensor comprises a plurality of sensors and the injector further comprises a testing mechanism to test the operation of each of the plurality of sensors.

30. The injector of claim 29 wherein the testing mechanism comprises a plurality of testing light sources, each of the testing light sources being adapted to transmit light to one of the plurality of sensors.

31. The injector of claim 19 wherein the injector comprises a plurality of sensors.

32. The injector of claim 31 wherein each of the plurality of sensors is adapted to sense light impinging thereon which is redirected from a unique axial position on the syringe or the syringe adapter.

33. The injector of claim 19 wherein the light source is operable to propagate light along an inner surface of a wall of the syringe or the syringe adapter in an axial direction.

34. The injector of claim 19 wherein the tight source is operable to propagate light along an outer surface of a wall of the syringe or the syringe adapter in an axial direction.

35. The injector of claim 25 wherein the sensor assembly further comprises a testing light source for each sensor to test the operability of each sensor.

* * * * *

UNITED STATES PATENT AND TRADEMARK OFFICE
CERTIFICATE OF CORRECTION

| | | |
|---|---|---|
| PATENT NO. | : 7,462,166 B2 | Page 1 of 1 |
| APPLICATION NO. | : 10/466418 | |
| DATED | : December 9, 2008 | |
| INVENTOR(S) | : Kevin P. Cowan | |

It is certified that error appears in the above-identified patent and that said Letters Patent is hereby corrected as shown below:

ON THE FACE PAGE ITEM [57]

In the ABSTRACT, Line 1, delete "inclides" and insert -- includes --, therefor.

Column 9, Line 48, delete "procedures" and insert -- procedures. --, therefor.

Column 10, Line 47, delete "therethough" and insert -- therethrough --, therefor.

Column 13, Line 32, delete "xcited" and insert -- excited --, therefor.

Column 16, Line 50, delete "11" and insert -- In --, therefor.

Column 16, Line 57, delete "115c" and insert -- 1115c --, therefor.

Column 20, Line 34, delete "450" and insert -- 45° --, therefor.

Column 22, Line 43, delete "1640;" and insert -- 1640. --, therefor.

In Column 24, Line 59, in Claim 34, delete "tight" and insert -- light --, therefor.

Signed and Sealed this

Sixteenth Day of June, 2009

JOHN DOLL
*Acting Director of the United States Patent and Trademark Office*